US009175109B1

(12) United States Patent
Kreischer et al.

(10) Patent No.: US 9,175,109 B1
(45) Date of Patent: Nov. 3, 2015

(54) OLIGOMERIZATION PROCESSES AND POLYMER COMPOSITIONS PRODUCED THEREFROM

(71) Applicant: Chevron Phillips Chemical Company LP, The Woodlands, TX (US)

(72) Inventors: Bruce E. Kreischer, Kingwood, TX (US); Paul J. DesLauriers, Owasso, OK (US); Ronald D. Knudsen, Bartlesville, OK (US); Vivek Rohatgi, Owasso, OK (US); Mark E. Lashier, The Woodlands, TX (US); R. Kim Perry, Montgomery, TX (US); Chung Ching Tso, Bartlesville, OK (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 14/282,086

(22) Filed: May 20, 2014

(51) Int. Cl.
    *C07C 2/24* (2006.01)
    *C08F 10/00* (2006.01)
    *C08L 23/02* (2006.01)
    *C08F 6/12* (2006.01)
    *C08F 6/10* (2006.01)

(52) U.S. Cl.
    CPC ... *C08F 6/12* (2013.01); *C07C 2/24* (2013.01); *C08F 6/10* (2013.01); *C08F 10/00* (2013.01); *C08L 23/02* (2013.01)

(58) Field of Classification Search
    CPC ............ C07C 2/24; C08F 10/00; C08L 23/02
    USPC .................................... 524/543; 585/18, 255
    See application file for complete search history.

(56) References Cited

U.S. PATENT DOCUMENTS

| 4,668,838 | A |   | 5/1987  | Briggs         |         |
|-----------|---|---|---------|----------------|---------|
| 4,777,315 | A |   | 10/1988 | Levine et al.  |         |
| 4,853,356 | A |   | 8/1989  | Briggs         |         |
| 5,182,333 | A |   | 1/1993  | Powers et al.  |         |
| 5,198,563 | A |   | 3/1993  | Reagen et al.  |         |
| 5,288,823 | A |   | 2/1994  | Reagan et al.  |         |
| 5,331,104 | A |   | 7/1994  | Reagen et al.  |         |
| 5,340,785 | A |   | 8/1994  | Reagen et al.  |         |
| 5,360,879 | A |   | 11/1994 | Reagen et al.  |         |
| 5,376,612 | A |   | 12/1994 | Reagen et al.  |         |
| 5,382,738 | A |   | 1/1995  | Reagen et al.  |         |
| 5,399,539 | A |   | 3/1995  | Reagen et al.  |         |
| 5,438,027 | A |   | 8/1995  | Reagen et al.  |         |
| 5,470,926 | A |   | 11/1995 | Reagen et al.  |         |
| 5,523,507 | A |   | 6/1996  | Reagen et al.  |         |
| 5,543,375 | A |   | 8/1996  | Lashier et al. |         |
| 5,563,312 | A |   | 10/1996 | Knudsen et al. |         |
| 5,689,028 | A |   | 11/1997 | Lashier et al. |         |
| 5,750,816 | A |   | 5/1998  | Araki et al.   |         |
| 5,763,723 | A |   | 6/1998  | Reagen et al.  |         |
| 5,814,575 | A |   | 9/1998  | Reagen et al.  |         |
| 5,856,257 | A |   | 1/1999  | Freeman et al. |         |
| 5,856,612 | A | * | 1/1999  | Araki et al.   | 585/522 |
| 5,859,303 | A |   | 1/1999  | Lashier        |         |
| 5,910,619 | A | * | 6/1999  | Urata et al.   | 585/513 |
| 6,133,495 | A |   | 10/2000 | Urata et al.   |         |
| 6,380,451 | B1|   | 4/2002  | Kreischer et al.|        |
| 6,455,648 | B1|   | 9/2002  | Freeman et al. |         |
| 7,157,612 | B2|   | 1/2007  | Ewert et al.   |         |
| 7,285,607 | B2|   | 10/2007 | Blann et al.   |         |
| 7,297,832 | B2|   | 11/2007 | Blann et al.   |         |
| 7,323,524 | B2|   | 1/2008  | Blann et al.   |         |
| 7,378,537 | B2|   | 5/2008  | Small et al.   |         |
| 7,384,886 | B2|   | 6/2008  | Knudsen et al. |         |
| 7,476,775 | B2|   | 1/2009  | Kreischer      |         |
| 7,511,183 | B2|   | 3/2009  | Blann et al.   |         |
| 7,525,009 | B2|   | 4/2009  | Blann et al.   |         |
| 7,718,838 | B2|   | 5/2010  | Woodard et al. |         |
| 7,820,581 | B2|   | 10/2010 | Knudsen et al. |         |
| 7,829,749 | B2|   | 11/2010 | Gao et al.     |         |
| 7,906,681 | B2|   | 3/2011  | Gao et al.     |         |
| 7,910,670 | B2|   | 3/2011  | Knudsen et al. |         |
| 7,964,763 | B2|   | 6/2011  | Dixon et al.   |         |
| 7,994,363 | B2|   | 8/2011  | Gao et al.     |         |
| 8,049,052 | B2|   | 11/2011 | Kreischer et al.|        |
| 8,076,523 | B2|   | 12/2011 | Bollmann et al.|         |
| 8,134,038 | B2|   | 3/2012  | McGuinness et al.|       |
| 8,252,955 | B2|   | 8/2012  | Gao et al.     |         |
| 8,252,956 | B2|   | 8/2012  | Gao et al.     |         |

(Continued)

FOREIGN PATENT DOCUMENTS

| EP | 608447       | A1 | 8/1994 |
| EP | 706983       | A1 | 4/1996 |
| EP | 0 881 237    |    | 5/1997 |
| WO | WO 03/016396 |    | 2/2003 |
| WO | WO 2013/013300|   | 1/2013 |
| WO | WO 2015/094207|   | 6/2015 |

OTHER PUBLICATIONS

*Modern Plastics Encyclopedia*, Mid-Nov. 1995 Issue, vol. 72, No. 12, 3 pages.
*Film Extrusion Manual—Process, Materials, Properties*, TAPPI Press, 1992, 16 pages.
Wool, Richard P., entitled "Polymer Interfaces—Surface and Strength," 1995, 3 pages.
Bicerano, Jozef, entitled "Prediction of Polymer Properties," third Edition, Revised and Expanded, 2002, 6 pages.
Van Krevelen, et al., entitled "Properties of Polymers, Their Correlation With Chemical Structure; Their Numerical Estimation and Prediction From Additive Group Contributions," 2009, 5 pages.

(Continued)

*Primary Examiner* — Ling Choi
*Assistant Examiner* — Ronald Grinsted
(74) *Attorney, Agent, or Firm* — Merchant & Gould P.C.

(57) ABSTRACT

Disclosed herein are methods for recovering a by-product stream of an ethylene oligomerization process, and systematically processing this stream in order to form a polymer composition that can be pelletized conventionally. This polymer composition can have a bimodal molecular weight distribution, which can be characterized by a ratio of the respective peak molecular weights ranging from 400:1 to 2000:1, and further, a liquid component of the polymer composition is in a range from 1 to 35 weight percent.

22 Claims, 13 Drawing Sheets

(56) References Cited

U.S. PATENT DOCUMENTS

| | | |
|---|---|---|
| 8,268,941 B2 | 9/2012 | Kleingeld et al. |
| 8,329,608 B2 | 12/2012 | Knudsen et al. |
| 8,334,420 B2 | 12/2012 | Small et al. |
| 8,344,198 B2 | 1/2013 | Ewert et al. |
| 8,367,786 B2 | 2/2013 | Dixon et al. |
| 8,461,406 B2 | 6/2013 | Overett et al. |
| 8,471,085 B2 | 6/2013 | Sydora |
| 8,680,003 B2 | 3/2014 | Sydora et al. |
| 2004/0236163 A1 | 11/2004 | Ewert et al. |
| 2009/0306442 A1 | 12/2009 | Pretorius et al. |
| 2010/0036185 A1 | 2/2010 | Yokoyama et al. |
| 2010/0113257 A1* | 5/2010 | Kreischer et al. .............. 502/161 |
| 2010/0113851 A1 | 5/2010 | Kreischer et al. |
| 2010/0113852 A1 | 5/2010 | Sydora |
| 2010/0331503 A1 | 12/2010 | Emoto et al. |
| 2011/0257350 A1 | 10/2011 | Jaber et al. |
| 2011/0282016 A1 | 11/2011 | Carter et al. |
| 2012/0041241 A1 | 2/2012 | Ewart et al. |
| 2012/0088933 A1 | 4/2012 | Carter et al. |
| 2012/0101321 A1 | 4/2012 | Brown et al. |
| 2012/0142989 A1 | 6/2012 | Jaber et al. |
| 2012/0199467 A1 | 8/2012 | Gildenhuys et al. |
| 2012/0271087 A1 | 10/2012 | Brown et al. |
| 2012/0316303 A1 | 12/2012 | Hanton et al. |
| 2013/0150605 A1 | 6/2013 | Sydora et al. |
| 2013/0150642 A1 | 6/2013 | Sydora et al. |
| 2013/0319131 A1 | 12/2013 | Inn et al. |
| 2013/0331629 A1 | 12/2013 | Sydora et al. |

OTHER PUBLICATIONS

Briggs, John R. entitled "The Selective Trimerization of Ethylene to Hex-1-ene," published in the J. Chem. Soc., Chem Commun., 1989, pp. 674-675.

International Search Report dated Jul. 28, 2015 cited in Application No. PCT/US2015/031474, 5 pgs.

* cited by examiner

OLIGOMERIZATION PROCESSES AND POLYMER COMPOSITIONS PRODUCED THEREFROM

BACKGROUND OF THE INVENTION

The oligomerization of ethylene to produce hexenes and/or octenes often can produce a by-product stream containing a heavy oligomer fraction and a polymeric fraction, as well as deactivated and/or catalyst system residue. It would be beneficial to treat and recover the polymeric fraction to reduce waste, and to use the treated and recovered compositions in a variety of end-use applications. Accordingly, it is to these ends that the present invention is directed.

SUMMARY OF THE INVENTION

This summary is provided to introduce a selection of concepts in a simplified form that are further described below in the detailed description. This summary is not intended to identify required or essential features of the claimed subject matter. Nor is this summary intended to be used to limit the scope of the claimed subject matter.

Embodiments of this invention are directed to a process comprising (1) contacting ethylene, a catalyst system comprising a transition metal compound and a metal alkyl, and an optional oligomerization diluent in a reactor under oligomerization conditions to form an oligomer product; (2) removing a reactor effluent from the reactor; (3) deactivating the catalyst system, e.g., to produce a deactivated reactor effluent; (4) isolating a heavies stream comprising a liquid fraction and a solid fraction; and (5) removing at least a portion of the liquid fraction from the heavies stream to produce the polymer composition. In some embodiments, the process can be a process for producing a polymer composition from a by-product stream of an oligomerization process as disclosed herein. Consistent with embodiments of this invention, the reactor effluent (or the deactivated reactor effluent) can comprise (i) ethylene; (ii) an oligomer product comprising (a) a light oligomer; (b) a specified oligomer that is at least 70 wt. % of the oligomer product, the specified oligomer comprising hexenes and/or octenes; (c) a heavy oligomer; and (d) a polymer; and (iii) an optional oligomerization diluent. The processes disclosed herein can further comprise a step of forming polymer pellets from the polymer composition, for example, using an extruder or gear pump and a pelletizing die. Unexpectedly, particularly given the significant liquid content of the polymer composition, the processes described herein can produce polymer pellets from the polymer composition derived from the by-products of the ethylene oligomerization process.

The compositions provided herein often can have a bimodal molecular weight distribution, which can be characterized by a ratio of the respective peak molecular weights ranging from 400:1 to 2000:1, and further, a liquid component of such compositions can range from 1 to 35 weight percent of the composition. A representative and non-limiting example of a composition (e.g., a polymer composition) consistent with embodiments of this invention can comprise a (a) high molecular weight hydrocarbon polymer component and a low molecular weight hydrocarbon oligomer component, wherein a ratio of the Mp of the high molecular weight hydrocarbon polymer component to the Mp of the low molecular weight hydrocarbon oligomer component can be in a range from 400:1 to 2000:1; and (b) a liquid component in a range from 1 wt. % to 35 wt. % of the composition, the liquid component comprising saturated hydrocarbon compounds having 16 or less carbon atoms and unsaturated hydrocarbon compounds having 18 or less carbon atoms. Another representative and non-limiting example of a composition consistent with embodiments of this invention can comprise (a) a high molecular weight hydrocarbon polymer component and a low molecular weight hydrocarbon oligomer component, wherein a ratio of the Mp of the high molecular weight hydrocarbon polymer component to the Mp of the low molecular weight hydrocarbon oligomer component can be in a range from 400:1 to 2000:1; and (b) a TGA (thermogravimetric analysis) liquid component in a range from 1 wt. % to 35 wt. % of the composition. Yet another representative and non-limiting example of a composition consistent with embodiments of this invention can comprise (a) a high molecular weight hydrocarbon polymer component and a low molecular weight hydrocarbon oligomer component, wherein a ratio of the Mp of the high molecular weight hydrocarbon polymer component to the Mp of the low molecular weight hydrocarbon oligomer component can be in a range from 400:1 to 2000:1; and (b) a DSC (differential scanning calorimeter) liquid component in a range from 1 wt. % to 35 wt. % of the composition. Surprisingly, these compositions, despite a significant liquid component, can be melt processed to produce conventional polymer pellets, which can subsequently be used to form various articles of manufacture.

Both the foregoing summary and the following detailed description provide examples and are explanatory only. Accordingly, the foregoing summary and the following detailed description should not be considered to be restrictive. Further, features or variations may be provided in addition to those set forth herein. For example, certain aspects and embodiments may be directed to various feature combinations and sub-combinations described in the detailed description.

BRIEF DESCRIPTION OF THE FIGURES

The accompanying drawings, which are incorporated in and constitute a part of this disclosure, illustrate various embodiments of the present invention. In the drawings.

DEFINITIONS

Figures 1, 2:
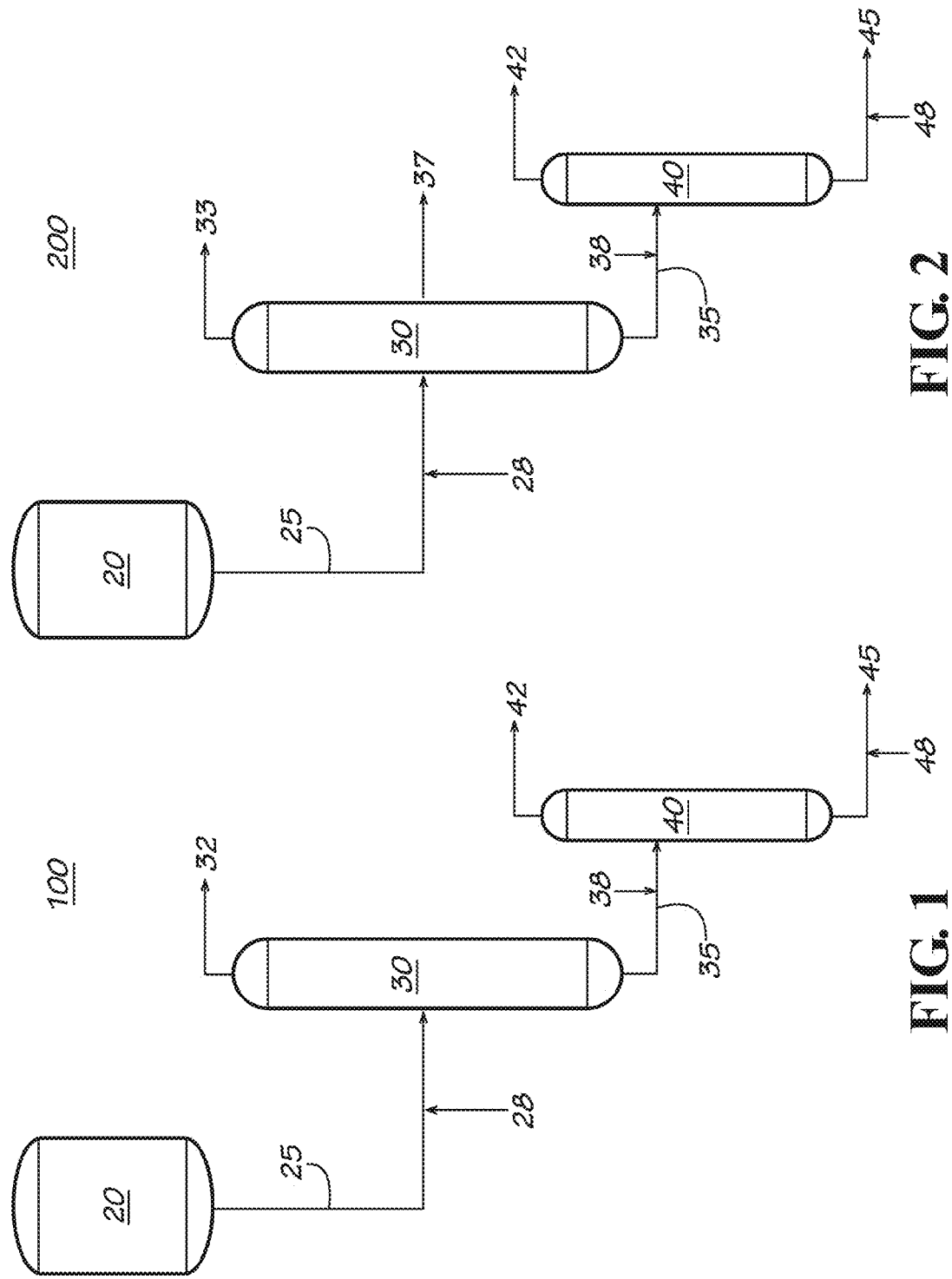
FIG. 1 presents a schematic diagram of a process in an embodiment of the present invention.
FIG. 2 presents a schematic diagram of a process in another embodiment of the present invention.

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, 2nd Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Herein, features of the subject matter can be described such that, within particular aspects and/or embodiments, a combination of different features can be envisioned. For each and every aspect, and/or embodiment, and/or feature disclosed herein, all combinations that do not detrimentally affect the designs, compositions, processes, and/or methods described herein are contemplated with or without explicit description of the particular combination. Additionally, unless explicitly recited otherwise, any aspect, and/or embodiment, and/or feature disclosed herein can be combined to describe inventive features consistent with the present disclosure.

Regarding claim transitional terms or phrases, the transitional term "comprising," which is synonymous with "including," "containing," "having," or "characterized by," is open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps and those that do not materially affect the basic and novel characteristics of the claimed invention. A "consisting essentially of" claim occupies a middle ground between closed claims that are written in a "consisting of" format and fully open claims that are drafted in a "comprising" format. Absent an indication to the contrary, describing a composition or method as "consisting essentially of" is not to be construed as "comprising," but is intended to describe the recited element that includes materials or steps which do not significantly alter the composition or method to which the term is applied. For example, a feedstock consisting essentially of a material A can include impurities typically present in a commercially produced or commercially available sample of the recited compound or composition. When a claim includes different features and/or feature classes (for example, a method step, feedstock features, and/or product features, among other possibilities), the transitional terms comprising, consisting essentially of, and consisting of apply only to the feature class to which it is utilized, and it is possible to have different transitional terms or phrases utilized with different features within a claim. For example, a method can comprise several recited steps (and other non-recited steps), but utilize a product stream consisting of specific components; alternatively, consisting essentially of specific components; or alternatively, comprising the specific components and other non-recited components. While compositions and methods are described in terms of "comprising" various components or steps, the compositions and methods can also "consist essentially of" or "consist of" the various components or steps, unless specifically stated otherwise. For example, a composition consistent with certain embodiments of the present invention can comprise (or can be characterized by); alternatively, consist essentially of or alternatively, consist of a high molecular weight hydrocarbon polymer component and a low molecular weight hydrocarbon oligomer component, and a liquid component ranging from 1 wt. % to 35 wt. % of the composition.

The terms "a," "an," and "the" are intended to include plural alternatives, e.g., at least one, unless otherwise specified. For instance, the disclosure of "a separation step" is meant to encompass one, or combinations of more than one, separation step (e.g., a flash process, a distillation process, etc.), unless otherwise specified.

Generally, groups of elements are indicated using the numbering scheme indicated in the version of the periodic table of elements published in *Chemical and Engineering News*, 63(5), 27, 1985. In some instances, a group of elements can be indicated using a common name assigned to the group; for example, alkali metals for Group 1 elements, alkaline earth metals for Group 2 elements, transition metals for Group 3-12 elements, and halogens or halides for Group 17 elements.

For any particular compound or group disclosed herein, any name or structure presented is intended to encompass all conformational isomers, regioisomers, stereoisomers, and mixtures thereof that can arise from a particular set of substituents, unless otherwise specified. The name or structure also encompasses all enantiomers, diastereomers, and other optical isomers (if there are any), whether in enantiomeric or racemic forms, as well as mixtures of stereoisomers, as would be recognized by a skilled artisan, unless otherwise specified. For example, a general reference to hexene (or hexenes) includes all linear or branched, acyclic or cyclic, hydrocarbon compounds having six carbon atoms and 1 carbon-carbon double bond; pentane includes n-pentane, 2-methyl-butane, and 2,2-dimethylpropane; a general reference to a butyl group includes an n-butyl group, a sec-butyl group, an iso-butyl group, and a t-butyl group; a general reference to cyclododecatriene includes all isomeric forms (e.g., trans,trans,cis-1,5,9-cyclododecatriene, and trans,trans,trans-1,5,9-cyclododecatriene, among other dodecatrienes); and a general reference to 2,3-pentanediol includes 2R,3R-pentanediol, 2S,3S-pentanediol, 2R,3S-pentanediol, and mixtures thereof.

The terms "contact product," "contacting," and the like, are used herein to describe compositions and methods wherein the components are contacted together in any order, in any manner, and for any length of time. For example, the components can be contacted by blending or mixing. Further, unless otherwise specified, the contacting of any component can occur in the presence or absence of any other component of the compositions and methods described herein. Combining additional materials or components can be done by any suitable method. Further, the term "contact product" includes mixtures, blends, solutions, slurries, reaction products, and the like, or combinations thereof. Although "contact product" can, and often does, include reaction products, it is not required for the respective components to react with one another. Similarly, the term "contacting" is used herein to refer to materials which can be blended, mixed, slurried, dissolved, reacted, treated, or otherwise contacted in some other manner. Hence, "contacting" two or more components can result in a mixture, a reaction product, a reaction mixture, etc.

The term "hydrocarbon" whenever used in this specification and claims refers to a compound containing only carbon and hydrogen. The term "olefin" as used herein refers to compound that has at least one carbon-carbon double bond that is not part of an aromatic ring or ring system. The term "olefin" includes aliphatic and aromatic, cyclic and acyclic, and/or linear and branched compounds having at least one carbon-carbon double bond that is not part of an aromatic ring or ring system, unless specifically stated otherwise. The term "olefin," by itself, does not indicate the presence or absence of heteroatoms and/or the presence or absence of other carbon-carbon double bonds unless explicitly indicated. The terms "hydrocarbon olefin" and "olefin hydrocarbon" refer to olefin compounds containing only hydrogen and carbon.

The terms "oligomerization product" and "oligomer product" include all products made by the "oligomerization" process including the "oligomers" and products which are not "oligomers" (e.g., polymer). The term "oligomer" refers to the portion of the oligomer product (saturated or unsaturated) having a molecular weight less than 3,400 g/mol, while the term "polymer" refers to the portion of the oligomer product (saturated or unsaturated) having a molecular weight of 3,400 g/mol or more. While the distinction between "oligomer" and "polymer" may seem arbitrary, the 3,400 g/mol value is based upon a two significant figure average of three published values (2844 g/mol, 3500 g/mol, and 4000 g/mol) of the critical molecular weight for polyethylene. See Wool, Polymer Interfaces-Surface and Strength, 1995, p. 5; Bicerano, Prediction of Polymer Properties, 2002, p. 502-505; and Van Krevelen, Properties of Polymers, 2009.

The term "oligomerization," and its derivatives, refers to processes which produce a mixture of products comprising at least 70 wt. % products comprising from 2 to 30 monomer units. In an example, an "oligomerization" process using ethylene as the monomer produces a mixture of products comprising at least 70 wt. % oligomers having from 4 to 60 carbon atoms.

The term "trimerization," and it derivatives, refers to a process which produces a mixture of products comprising at least 70 wt. % products comprising three and only three monomer units. A "trimer" is a product which comprises three and only three monomer units, while a "trimerization product" includes all products made by the trimerization process including trimer and product(s) which are not trimer (e.g., dimers or tetramers). In an example, a "trimerization" process using ethylene as the monomer produces a mixture of products comprising at least 70 wt. % hexenes.

The term "tetramerization," and it derivatives, refers to a process which produces a mixture of products comprising at least 70 wt. % products comprising four and only four monomer units. A "tetramer" is a product which comprises four and only four monomer units, while a "tetramerization product" includes all products made by the tetramerization process including tetramer and product(s) which are not tetramer (e.g., dimers or trimer). In an example, a "tetramerization" process using ethylene as the monomer produces a mixture of products comprising at least 70 wt. % octenes.

The term "trimerization and tetramerization," and it derivatives, refers to a process which produces a mixture of products comprising at least 70 wt. % products comprising three and/or four and only three and/or four monomer units. A "trimerization and tetramerization product" includes all products made by the "trimerization and tetramerization" process including trimer, tetramer, and product(s) which are not trimer and tetramer (e.g., dimers). In an example, a "trimerization and tetramerization" process using ethylene as the monomer produces a mixture of products comprising at least 70 wt. % hexenes and/or octenes.

Although any methods and materials similar or equivalent to those described herein can be used in the practice or testing of the invention, the typical methods and materials are herein described.

All publications and patents mentioned herein are incorporated herein by reference for the purpose of describing and disclosing, for example, the constructs and methodologies that are described in the publications, which might be used in connection with the presently described invention. The publications discussed throughout the text are provided solely for their disclosure prior to the filing date of the present application. Nothing herein is to be construed as an admission that the inventors are not entitled to antedate such disclosure by virtue of prior invention.

DETAILED DESCRIPTION OF THE INVENTION

The following detailed description refers to the accompanying drawings. Wherever possible, the same or similar reference numbers are used in the drawings and the following description to refer to the same or similar elements or features. While various embodiments of the invention are described, modifications, adaptations, and other implementations are possible. For example, substitutions, additions, or modifications can be made to the elements illustrated in the drawings, and the methods described herein can be modified by substituting, reordering, or adding stages to the disclosed methods. Accordingly, the following detailed description and its exemplary embodiments do not limit the scope of the invention.

Compositions

In particular embodiments of this invention, the compositions (e.g., polymer compositions) disclosed herein often can have a bimodal molecular weight distribution, which can be characterized by a ratio of the respective peak molecular weights, Mp, ranging from 400:1 to 2000:1, and further, a liquid component of such compositions can range from 1 to 35 weight percent of the composition. For instance, an illustrative and non-limiting example of a composition consistent with embodiments of this invention can be characterized by a (a) high molecular weight hydrocarbon polymer component and a low molecular weight hydrocarbon oligomer component, wherein a ratio of the Mp of the high molecular weight hydrocarbon polymer component to the Mp of the low molecular weight hydrocarbon oligomer component can be in a range from 400:1 to 2000:1; and (b) a liquid component in a range from 1 wt. % to 35 wt. % of the composition, the liquid component comprising saturated hydrocarbon compounds having 16 or less carbon atoms and unsaturated hydrocarbon compounds having 18 or less carbon atoms. Compounds included in this liquid component include any compounds which, as a pure compound, are liquids (not solids or gasses) at standard temperature (25° C.) and pressure (1 atm). For instance, $C_{16}$ and $C_{18}$ olefins are liquids at standard temperature and pressure, while linear octadecane is not a liquid at standard temperature and pressure and, therefore, is not considered to be part of the liquid component of the composition. It should be noted that materials other than hydrocarbons can be present in the liquid component.

All molecular weights (Mp is the peak molecular weight, Mn is the number-average molecular weight, Mw is the weight-average molecular weight, and Mz is the z-average molecular weight) relating to the compositions disclosed herein were determined using the GPC procedure described herein using the molecular weight standards described herein. Moreover, as described further herein, the low molecular weight hydrocarbon oligomer component of the composition can comprise most of the liquid component; however, due to limitations in utilized GPC analytical techniques, liquid materials with molecular weights under 200 g/mol are not included in the low molecular weight hydrocarbon oligomer component of the overall composition.

The test procedure for the liquid component first involves treatment of the composition with xylene to produce a xylene soluble fraction of the composition and a xylene insoluble fraction of the composition, as described herein below. The xylene soluble fraction comprises predominantly materials having molecular weights of less than about 3000 g/mol. The test for the amount of the liquid component utilizes the xylene soluble fraction (and the percentage amount of the composition encompassed by the xylene soluble fraction) and the GC or GC-MS analytical procedure/equipment disclosed herein to determine the weight percentage of compounds in the composition that are liquids at standard temperature and pressure.

In an embodiment, the liquid component of the composition can comprise at least 50 wt. %, 60 wt. %, 70 wt. %, 75 wt. %, 80 wt. %, 85 wt. %, 90 wt. %, or 95 wt. %, liquid compounds having at least 12 carbon atoms. In another embodiment, the liquid component of the composition can comprise at least 50 wt. %, 60 wt. %, 70 wt. %, 75 wt. %, 80 wt. %, 85 wt. %, 90 wt. %, or 95 wt. %, liquid compounds having at least 14 carbon atoms.

Another illustrative and non-limiting example of a composition consistent with embodiments of this invention can be characterized by (a) a high molecular weight hydrocarbon polymer component and a low molecular weight hydrocarbon oligomer component, wherein a ratio of the Mp of the high molecular weight hydrocarbon polymer component to the Mp of the low molecular weight hydrocarbon oligomer component can be in a range from 400:1 to 2000:1; and (b) a TGA liquid component in a range from 1 wt. % to 35 wt. % of the composition. The amount of the TGA liquid component in the composition is the amount of weight lost (calculated on the basis of the entire composition) from the composition (or from the xylene soluble fraction of the composition) from 0° C. to 240° C. during a TGA analysis run from 0° C. to 600° C., using the analytical procedure/equipment disclosed herein.

Yet another illustrative and non-limiting example of a composition consistent with embodiments of this invention can be characterized by (a) a high molecular weight hydrocarbon polymer component and a low molecular weight hydrocarbon oligomer component, wherein a ratio of the Mp of the high molecular weight hydrocarbon polymer component to the Mp of the low molecular weight hydrocarbon oligomer component can be in a range from 400:1 to 2000:1; and (b) a DSC liquid component in a range from 1 wt. % to 35 wt. % of the composition. The amount of the DSC liquid component in the composition is the amount (calculated on the basis of the entire composition) of the composition (or the xylene soluble fraction of the composition) that has a DSC phase transition at atmospheric pressure of less than or equal to 25° C., using the analytical procedure/equipment disclosed herein.

These illustrative and non-limiting examples of compositions—comprising a high molecular weight hydrocarbon polymer component, a low molecular weight hydrocarbon oligomer component, and a certain percentage that is a liquid component—consistent with the present invention also can have any of the characteristics or polymer properties provided below, and in any combination.

As would be recognized by those of skill in the art, while the liquid component, the TGA liquid component, and the DSC liquid component are similar in composition (and constitute mostly the same materials), the analytical methods utilized do not measure the exact same materials and respective amounts. Consequently, there can be variations between the materials included in these three different "liquid" components and, therefore, the values of the weight percentages can be different between these analytical procedures. Accordingly, each of the liquid component, the TGA liquid component, and the DSC liquid component, independently, can encompass from 1 wt. % to 35 wt. % of the composition, but the exact weight percentages can vary.

Hence, consistent with embodiments of the present invention, the percentage of the liquid component (or the TGA liquid component, or the DSC liquid component) of the composition typically ranges from 1 wt. % to 35 wt. % of the composition. In some embodiments, for instance, the minimum weight percentage of the liquid component (or the TGA liquid component, or the DSC liquid component) of the composition can be 1 wt. %, 2 wt. %, 3 wt. %, 4 wt. %, 5 wt. %, 5 wt. %, 8 wt. %, or 10 wt. %; additionally or alternatively, a maximum weight percentage of the liquid component (or the TGA liquid component, or the DSC liquid component) of the composition can be 35 wt. %, 32 wt. %, 30 wt. %, 28 wt. %, 25 wt. %, or 20 wt. %. Generally, the weight percentage of the liquid component (or the TGA liquid component, or the DSC liquid component) of the composition can be in a range from any minimum weight percentage disclosed herein to any maximum weight percentage disclosed herein. Therefore, the weight percentage of the liquid component (or the TGA liquid component, or the DSC liquid component) of the composition can be in the following non-limiting ranges: from 1 wt. % to 35 wt. %, from 1 wt. % to 30 wt. %, from 1 wt. % to 25 wt. %, from 2 wt. % to 35 wt. %, from 2 wt. % to 25 wt. %, from 5 wt. % to 35 wt. %, from 5 wt. % to 30 wt. %, from 5 wt. % to 25 wt. %, from 7 wt. % to 35 wt. %, from 10 wt. % to 35 wt. %, from 10 wt. % to 30 wt. %, or from 10 wt. % to 25 wt. %. Other appropriate ranges for the amount of the liquid component (or the TGA liquid component, or the DSC liquid component) of the composition are readily apparent from this disclosure.

In some embodiments, the high molecular weight hydrocarbon polymer component, the low molecular weight hydrocarbon oligomer component, and the liquid component (or TGA liquid component, or DSC liquid component) can comprise at least 88 wt. % of the (total) composition. In other embodiments, the weight percentage of the composition encompassed by the high molecular weight hydrocarbon polymer component, the low molecular weight hydrocarbon oligomer component, and the liquid component (or TGA liquid component, or DSC liquid component) can be at least 90 wt. %, at least 92 wt. %, at least 95 wt. %, or at least 96 wt. % of the (total) composition.

Compositions consistent with embodiments of the present invention generally can have a ratio of the Mp of the high molecular weight hydrocarbon polymer component to the Mp of the low molecular weight hydrocarbon oligomer component in a range from 400:1 to 2000:1. For example, in some embodiments, the ratio of the Mp of the high molecular weight hydrocarbon polymer component to the Mp of the low molecular weight hydrocarbon oligomer can be at least 50:1, 100:1, 200:1, 400:1, 500:1, 600:1, 700:1, 800:1, 900:1, or 1000:1; additionally or alternatively, less than or equal to 7,500:1, 6,000:1, 5,000:1, 4,000:1, 3,000:1, 2,000:1, 1800:1, 1600:1, 1500:1, 1400:1, 1300:1, 1200:1, or 1100:1. Generally, the ratio of the Mp of the high molecular weight hydrocarbon polymer component to the Mp of the low molecular weight hydrocarbon oligomer can be in a range from any minimum ratio disclosed herein to any maximum ratio disclosed herein. Therefore, suitable non-limiting ranges for the ratio of the Mp of the high molecular weight hydrocarbon polymer component to the Mp of the low molecular weight hydrocarbon oligomer can include the following ranges: from 50:1 to 7,500:1, from 100:1 to 6,000:1, from 100:1 to 5,000:1, from 200:1 to 5,000:1, from 200:1 to 4,000:1, from 200:1 to 3,000:1, from 400:1 to 1800:1, from 500:1 to 2,000:1, from 500:1 to 1500:1, from 600:1 to 1600:1, from 600:1 to 1400:1, from 700:1 to 1300:1, or from 800:1 to 1200:1. Other appropriate ranges for the ratio of the Mp of the high molecular weight hydrocarbon polymer component to the Mp of the low molecular weight hydrocarbon oligomer are readily apparent from this disclosure.

In an embodiment, the low molecular weight hydrocarbon oligomer component can have a Mp in a range from 200 to 2500 g/mol. For instance, the Mp of the low molecular weight hydrocarbon oligomer can be at least 200, 225, 250, 275, 300, 325, 350, or 400 g/mol; additionally or alternatively, less than or equal to 2500, 2000, 1800, 1500, 1250, 1000, 750, 650, 600, 550, or 500 g/mol. Generally, the Mp of the low molecular weight hydrocarbon oligomer component can be in a range from any minimum peak molecular weight disclosed herein to any maximum peak molecular weight disclosed herein. Therefore, suitable non-limiting ranges for the Mp of the low molecular weight hydrocarbon oligomer component can include the following ranges: from 200 to 2500, from 250 to 2500, from 250 to 2000, from 250 to 1500, from 250 to 1000, from 250 to 750, from 250 to 600, from 300 to 2000, from 300 to 1500, from 300 to 1000, from 300 to 700, from 350 to 1800, from 350 to 1250, from 350 to 750, or from 350 to 550 g/mol. Other appropriate ranges for the Mp of the low molecular weight hydrocarbon oligomer component are readily apparent from this disclosure. Furthermore, in some embodiments, the low molecular weight hydrocarbon oligomer component can comprise liquid materials (e.g., liquid oligomers) having molecular weights over 200 g/mol, and solid oligomer materials generally with molecular weights of less than 3400 g/mol.

In an embodiment, the high molecular weight hydrocarbon polymer component can have an Mp in a range from 150,000 to 1,000,000 g/mol. For instance, the Mp of the high molecular weight hydrocarbon polymer can be at least 150,000, 200,000, 225,000, 250,000, 275,000, 300,000, 325,000, or 350,000 g/mol; additionally or alternatively, less than or equal to 1,000,000, 900,000, 800,000, 750,000, 700,000, 650,000, 600,000, 550,000, or 500,000 g/mol. Generally, the Mp of the high molecular weight hydrocarbon polymer component can be in a range from any minimum peak molecular weight disclosed herein to any maximum peak molecular weight disclosed herein. Therefore, suitable non-limiting ranges for the Mp of the high molecular weight hydrocarbon polymer component can include the following ranges: from 150,000 to 1,000,000, from 150,000 to 750,000, from 200,000 to 900,000, from 200,000 to 750,000, from 200,000 to 600,000, from 200,000 to 500,000, from 250,000 to 1,000,000, from 250,000 to 750,000, from 250,000 to 550,000, from 300,000 to 900,000, from 300,000 to 750,000, from 300,000 to 500,000, or from 325,000 to 650,000 g/mol. Other appropriate ranges for the Mp of the high molecular weight hydrocarbon polymer component are readily apparent from this disclosure. Furthermore, in some embodiments, the high molecular weight hydrocarbon polymer component can comprise ethylene/α-olefin copolymers, such as, for example, a mixture of polymer chains incorporating various length olefin comonomers.

Compositions consistent with embodiments of the present invention generally can have a ratio of Mw/Mn, or the polydispersity index, in a range from 50 to 200. For example, in some embodiments, the Mw/Mn can be at least 50, 60, 70, 80, 90, or 100; additionally or alternatively, less than or equal to 200, 190, 180, 170, 160, 150, or 140. Generally, the Mw/Mn of the composition can be in a range from any minimum Mw/Mn disclosed herein to any maximum Mw/Mn disclosed herein. Therefore, suitable non-limiting ranges for Mw/Mn of the composition can include the following ranges: from 60 to 200, from 70 to 200, from 70 to 170, from 90 to 190, from 90 to 170, from 80 to 200, from 80 to 180, from 80 to 160, from 100 to 200, from 100 to 180, from 100 to 160, or from 100 to 160. Other appropriate ranges for the Mw/Mn of the composition are readily apparent from this disclosure.

Compositions consistent with embodiments of the present invention generally can have a ratio of Mz/Mw in a range from 3 to 15. For example, in some embodiments, the Mz/Mw can be at least 3, 3.5, 4, 4.5, 5, 5.5, or 6; additionally or alternatively, less than or equal to 15, 14, 13, 12, 11, 10, or 9. Generally, the Mz/Mw of the composition can be in a range from any minimum Mz/Mw disclosed herein to any maximum Mz/Mw disclosed herein. Therefore, suitable non-limiting ranges for Mz/Mw of the composition can include the following ranges: from 3 to 14, from 3 to 12, from 3 to 10, from 3 to 8, from 4 to 14, from 4 to 12, from 4 to 10, from 5 to 15, from 5 to 12, from 5 to 10, from 6 to 14, or from 6 to 9. Other appropriate ranges for the Mz/Mw of the composition are readily apparent from this disclosure.

In an embodiment, the composition can have an Mw in a range from 25,000 to 300,000 g/mol. For instance, the Mw of the composition can be at least 25,000, 30,000, 35,000, 40,000, 45,000, 50,000, or 60,000 g/mol; additionally or alternatively, less than or equal to 300,000, 250,000, 200,000, 175,000, 150,000, 130,000, 120,000, or 110,000 g/mol. Generally, the Mw of the composition can be in a range from any minimum Mw disclosed herein to any maximum Mw disclosed herein. Therefore, suitable non-limiting ranges for the Mw of the composition can include the following ranges: from 25,000 to 250,000, from 30,000 to 200,000, from 30,000 to 130,000, from 40,000 to 175,000, from 40,000 to 150,000, from 40,000 to 120,000, from 50,000 to 150,000, or from 60,000 to 160,000 g/mol. Other appropriate ranges for the Mw of the composition are readily apparent from this disclosure.

In an embodiment, the composition can have an Mn in a range from 200 to 2500 g/mol. For instance, the Mn of the composition can be at least 200, 225, 250, 275, 300, 350, or 400 g/mol; additionally or alternatively, less than or equal to 2500, 2000, 1750, 1500, 1250, 1100, 1000, or 900 g/mol. Generally, the Mn of the composition can be in a range from any minimum Mn disclosed herein to any maximum Mn disclosed herein. Therefore, suitable non-limiting ranges for the Mn of the composition can include the following ranges: from 250 to 2500, from 250 to 1500, from 250 to 1000, from 300 to 2000, from 300 to 1500, from 300 to 1000, from 400 to 1500, from 400 to 1250, from 400 to 1000, or from 400 to 900 g/mol. Other appropriate ranges for the Mn of the composition are readily apparent from this disclosure.

In an embodiment, the composition can have an Mz in a range from 300,000 to 1,000,000 g/mol. For instance, the Mz of the composition can be at least 300,000, 325,000, 350,000, 375,000, 400,000, 425,000, or 500,000 g/mol; additionally or alternatively, less than or equal to 1,000,000, 900,000, 800,000, 750,000, 700,000, 650,000, or 600,000 g/mol. Generally, the Mz of the composition can be in a range from any minimum Mz disclosed herein to any maximum Mz disclosed herein. Therefore, suitable non-limiting ranges for the Mz of the composition can include the following ranges: from 300,000 to 800,000, from 300,000 to 700,000, from 350,000 to 900,000, from 350,000 to 750,000, from 350,000 to 650,000, from 400,000 to 1,000,000, from 400,000 to 700,000, or from 400,000 to 600,000 g/mol. Other appropriate ranges for the Mz of the composition are readily apparent from this disclosure.

Compositions, such as polymer compositions, consistent with certain embodiments of the invention often can have a bimodal molecular weight distribution (as determined using gel permeation chromatography (GPC) or other suitable analytical technique). Often, in a bimodal molecular weight distribution, there is a valley between the peaks, and the peaks can be separated or deconvoluted. Typically, a bimodal molecular weight distribution can be characterized as having an identifiable high molecular weight component (or distribution) and an identifiable low molecular weight component (or distribution).

In an embodiment, the composition described herein can be a single reactor product or a single product stream, for example, a homogeneous mixture, not a blend of two polymeric/oligomeric components, for instance, having different molecular weight characteristics. As one of skill in the art would readily recognize, physical blends of two different materials or components can be made, but this necessitates additional processing and complexity not required for a single reactor product or single reactor stream. Additionally, the low molecular weight component can be comprised of a majority of a single reactor product or product stream (e.g., at least 50 wt. %, 60 wt. %, 70 wt. %, 75 wt. %, 80 wt. %, 85 wt. %, 90 wt. %, 95 wt. % of the low molecular weight component) and not a physical blend of oligomeric components and/or a physical blend of oligomeric component(s) and a solvent/diluent.

The density of the composition, inclusive of any metals and/or metal compounds that can be present, typically falls within a range from 0.92 to 1.02 g/cm$^3$. For instance, the density of the composition can be at least 0.92, at least 0.925, at least 0.93, at least 0.935, or at least 0.94 g/cm$^3$; additionally or alternatively, less than or equal to 1.02, 1.01, 1, 0.995, 0.99, 0.985, or 0.98 g/cm$^3$. Generally, the density of the composition can be in a range from any minimum density disclosed herein to any maximum density disclosed herein. Therefore, suitable non-limiting ranges for the density of the composition can include the following ranges: from 0.92 to 1.01, from 0.93 to 1, from 0.94 to 0.99, from 0.935 to 0.995, or from 0.94 to 0.98 g/cm$^3$. Other appropriate ranges for the density of the composition are readily apparent from this disclosure.

In an embodiment, the composition can comprise metal catalyst system components, deactivated metal catalyst system components, or any combination thereof; alternatively, metal catalyst system components; or alternatively, deactivated metal catalyst system components. For example, some catalyst systems which can result in the composition can comprise aluminum compounds and/or chromium compounds. In some embodiments, the composition can have an aluminum content of at least 0.5, 0.6, 0.7, 0.8, 0.9, 1.0, 1.1, or 1.2 wt. %; additionally or alternatively, an aluminum content of less than or equal to 10, 8, 7, 6, 5, 4.5, 4, 3.5, 3, 2.75, 2.5, 2.25, or 2 wt. %. Generally, the aluminum content of the composition can be in a range from any minimum aluminum content to any maximum aluminum content disclosed herein. Therefore, suitable non-limiting ranges for the composition's aluminum content can include the following ranges: from 0.5 wt. % to 10 wt. %, from 0.5 wt. % to 8 wt. %, from 0.5 wt. % to 6 wt. %, from 0.5 wt. % to 5 wt. %, from 0.5 wt. % to 4 wt. %, from 0.7 wt. % to 4 wt. %, from 1 wt. % to 4 wt. %, from 0.5 wt. % to 3.5 wt. %, from 0.5 wt. % to 3 wt. %, 0.5 wt. % to 2.5 wt. %, from 0.7 wt. % to 5 wt. %, from 0.7 wt. % to 3 wt. %, from 1 wt. % to 3 wt. %, or from 1 wt. % to 2.5 wt. %. Moreover, in some embodiments, the composition can have a chromium content of at least 0.05, 0.06, 0.07, 0.08, 0.09, or 0.1 wt. % chromium; additionally or alternatively, a chromium content less than or equal to 7, 5, 4, 3, 2, 1, 0.5, 0.4, 0.35, 0.3, 0.25, 0.2, or 0.18 wt. % chromium. Generally, the chromium content of the composition can be in a range from any minimum chromium content to any maximum chromium content disclosed herein. Therefore, suitable non-limiting ranges for the composition's chromium content can include the following ranges: from 0.05 wt. % to 7 wt. %, from 0.05 wt. % to 5 wt. %, from 0.05 wt. % to 4 wt. %, from 0.05 wt. % to 2 wt. %, from 0.05 wt. % to 1 wt. %, from 0.05 wt. % to 0.4 wt. %, from 0.05 wt. % to 0.25 wt. %, from 0.08 wt. % to 0.5 wt. %, from 0.08 wt. % to 0.3 wt. %, from 0.08 wt. % to 0.25 wt. %, from 0.08 wt. % to 0.2 wt. %, from 0.1 wt. % to 1 wt. %, from 0.1 wt. % to 0.5 wt. %, or from 0.1 wt. % to 0.3 wt. %. The aluminum content and/or chromium content of the composition are based upon the amount of aluminum and/or chromium in the total mass of the composition analyzed.

In some embodiments, the processes which produce the composition can utilize steps which can remove a portion or substantially all of the metal catalyst system components and/or the deactivated metal catalyst system components from the composition. Consequently, in other embodiments, the composition can be substantially devoid of metal. In some embodiments, the composition can be substantially devoid of aluminum and chromium; alternatively, substantially devoid of aluminum; or alternatively, substantially devoid of chromium. Within this application and claims, the composition substantially devoid of metal, substantially devoid of aluminum and chromium, substantially devoid of aluminum, or substantially devoid of chromium means that the composition can comprise a maximum metal, aluminum, and/or chromium content of 1000, 750, 500, 250, 100, 75, 50, 25, or 10 ppm (by weight). In some embodiments, for instance, the composition can comprise less than 500 ppm by weight of aluminum (or less than 100 ppm, or less than 50 ppm, in other embodiments) and less than 100 ppm by weight of chromium (or less than 50 ppm, or less than 25 ppm, in other embodiments).

In an embodiment, the composition can comprise non-combustible components (ash). In some embodiments, the composition can have an ash content of at least 0.1, 0.2, 0.5, 0.8, 1.0, 2.0, 2.5 or 3.0 wt. % ash; additionally or alternatively, an ash content less than or equal to 15, 13, 12, 10, or 9 wt. % ash. Therefore, suitable non-limiting ranges for the ash content in the composition can include the following ranges: from 0.1 wt. % to 15 wt. %, from 0.2 wt. % to 13 wt. %, from 0.5 wt. % to 13 wt. %, from 0.8 wt. % to 13 wt. %, from 1.0 wt. % to 12 wt. %, from 1.0 wt. % to 10 wt. %, from 2.0 wt. % to 15 wt. %, from 2.0 wt. % to 13 wt. %, from 2.5 wt. % to 15 wt. %, from 2.5 wt. % to 13 wt. %, or from 3 wt. % to 12 wt. %. Other appropriate ranges for the ash content of the composition are readily apparent from this disclosure. In other embodiments, the composition can be substantially devoid of ash (i.e., having a maximum ash content of 1000, 750, 500, 250, 100, 75, 50, 25, or 10 ppm by weight). Typically, ash is determined by burning a sample of the composition in an oven, in the presence of air, at a high temperature (typically greater than 600° C.) to burn off all the organic components, measuring the remaining mass of material after combustion, and reporting the remaining non-combustible material as a percentage of the original sample.

Additionally or alternatively, compositions consistent with embodiments of this invention can be characterized as having a xylene soluble fraction and a xylene insoluble fraction, using the analytical procedure/equipment disclosed herein. Often, the xylene soluble fraction can be at least 25, 27, 30, 32, 35, 37, or 40 wt. % of the composition; additionally or alternatively, less than or equal to 80, 75, 70, 65, 60, or 55 wt. % of the composition. Generally, the weight percentage of the xylene soluble fraction of the composition can range from any minimum amount to any maximum amount disclosed herein. Therefore, suitable non-limiting ranges for the amount of the xylene soluble fraction, based on the weight of the composition, can include the following ranges: from 25 wt. % to 80 wt. %, from 30 wt. % to 80 wt. %, from 35 wt. % to 80 wt. %, from 40 wt. % to 80 wt. %, from 30 wt. % to 70 wt. %, from 30 wt. % to 65 wt. %, from 35 wt. % to 70 wt. %, from 35 wt. % to 60 wt. %, from 35 wt. % to 55 wt. %, or from 40 wt. % to 65 wt. %. Other appropriate ranges for the amount of the xylene soluble fraction of the composition are readily apparent from this disclosure. It should be noted that the xylene soluble fraction, while containing a substantial portion of the low molecular weight hydrocarbon oligomer component, is not identical to the low molecular weight hydrocarbon oligomer component of the polymer composition. Similarly, the xylene insoluble fraction, while containing a substantial portion of the high molecular weight hydrocarbon polymer component, is not identical to the high molecular weight hydrocarbon polymer component of the polymer composition The xylene soluble fraction generally can comprise (1) liquid materials, i.e., materials that are liquids at standard temperature and pressure, and (2) oligomer materials, i.e., olefin-based oligomers having a Mp in a range from 250 to 1500 g/mol; or alternatively, from 250 to 1000, from 250 to 750, from 300 to 1500, from 300 to 1000, from 300 to 700, or from 300 to 550 g/mol. Other appropriate ranges for the Mp of the oligomer materials in the xylene soluble fraction are readily apparent from this disclosure. In further embodiments, the xylene soluble fraction can have a relatively high short chain branch (SCB) content and a relatively low long chain branch (LCB) content (greater than $C_6$). For instance, the number of SCB's per 1000 total carbon atoms can be in a range from 10 to 150, from 20 to 140, from 30 to 125, from 45 to 120, from 60 to 110, or from 65 to 105. The number of LCB's per 1000 total carbon atoms can be less than 0.01, less than 0.008, less than 0.007, less than 0.005, or less than 0.003.

The xylene soluble fraction, in certain embodiments, also can be characterized by a relatively narrow molecular weight distribution, such as by a ratio of Mw/Mn (or Mz/Mw) in a range from 1.01 to 3. For example, in some embodiments, the Mw/Mn (or Mz/Mw) of the xylene soluble fraction can be at least 1.01, 1.05, 1.1, 1.15, or 1.2; additionally or alternatively, less than or equal to 3, 2.5, 2, 1.75, or 1.5. Generally, the Mw/Mn (or Mz/Mw) of the xylene soluble fraction can be in a range from any minimum Mw/Mn (or Mz/Mw) disclosed herein to any maximum Mw/Mn (or Mz/Mw) disclosed herein. Therefore, suitable non-limiting ranges for the Mw/Mn (or Mz/Mw) of the xylene soluble fraction can include the following ranges: from 1.01 to 2.5, from 1.01 to 2, from 1.05 to 3, from 1.05 to 2.5, from 1.05 to 2, from 1.05 to 1.5, from 1.1 to 3, from 1.1 to 2.5, from 1.1 to 1.75, or from 1.1 to 1.5. Other appropriate ranges for the Mw/Mn (or Mz/Mw) of the xylene soluble fraction are readily apparent from this disclosure.

In an embodiment, the xylene soluble fraction can be characterized by a Mp (or Mn, or Mw, or Mz) in a range from 200 to 2500 g/mol. For instance, the Mp (or Mn, or Mw, or Mz) of the xylene soluble fraction can be at least 200, 225, 250, 275, 300, 325, 350, or 400 g/mol; additionally or alternatively, less than or equal to 2500, 2000, 1800, 1500, 1250, 1000, 750, 650, 600, 550, or 500 g/mol. Generally, the Mp (or Mn, or Mw, or Mz) of the xylene soluble fraction can be in a range from any minimum molecular weight disclosed herein to any maximum molecular weight of the xylene soluble fraction disclosed herein. Therefore, suitable non-limiting ranges for the Mp (or Mn, or Mw, or Mz) of the xylene soluble fraction can include the following ranges: from 200 to 2500, from 250 to 2500, from 250 to 2000, from 250 to 1500, from 250 to 1000, from 250 to 750, from 250 to 600, from 300 to 2000, from 300 to 1500, from 300 to 1000, from 300 to 700, from 350 to 1800, from 350 to 1250, from 350 to 750, or from 350 to 550 g/mol. Other appropriate ranges for the Mp (or Mn, or Mw, or Mz) of the xylene soluble fraction are readily apparent from this disclosure.

The DSC peak melting temperature of the xylene soluble fraction typically falls within a range from 10 to 60° C. For instance, the DSC peak melting temperature of the xylene soluble fraction of the composition can be at least 10, 11, 12, 13, 14, or 15° C.; additionally or alternatively, less than or equal to 60, 55, 45, 40, 35, 30, 25, or 20° C. Generally, the DSC peak melting temperature of the xylene soluble fraction can be in a range from any minimum DSC peak melting temperature of the xylene soluble fraction disclosed herein to any maximum DSC peak melting temperature of the xylene soluble fraction disclosed herein. Therefore, suitable non-limiting ranges for the DSC peak melting temperature of the xylene soluble fraction of the composition can include the following ranges: from 10 to 60, from 10 to 50, from 10 to 40, from 10 to 35, from 10 to 30, from 12 to 55, from 12 to 40, from 15 to 55, from 15 to 45, or from 15 to 30° C. Other appropriate ranges for the DSC peak melting temperature of the xylene soluble fraction are readily apparent from this disclosure.

The xylene insoluble fraction generally can comprise ethylene/α-olefin copolymers; these copolymers can have polymer chains incorporating various length olefin comonomers. Additionally, certain residual catalyst system components, such as chromium and aluminum, can be present in the xylene insoluble fraction. In further embodiments, the xylene insoluble fraction can have a short chain branch (SCB) content between 0 and 25 SCB's per 1000 total carbon atoms, and a low long chain branch (LCB) content of less than 0.05 LCB's per 1000 total carbon atoms. For instance, the number of SCB's per 1000 total carbon atoms can be in a range from 0 to 20, from 0.5 to 20, from 0.5 to 5, from 1 to 20, from 1 to 10, or from 1 to 5. The number of LCB's per 1000 total carbon atoms can be less than 0.01, less than 0.008, less than 0.005, in a range from 0.0005 to 0.025, in a range from 0.0005 to 0.01, or in a range from 0.0005 to 0.008.

The xylene insoluble fraction can have an Mp (or Mz) in a range from 150,000 to 1,000,000 g/mol. For instance, the Mp (or Mz) of the xylene insoluble fraction can be at least 150,000, 200,000, 225,000, 250,000, 275,000, 300,000, 325,000, or 350,000 g/mol; additionally or alternatively, less than or equal to 1,000,000, 900,000, 800,000, 750,000, 700,000, 650,000, 600,000, 550,000, or 500,000 g/mol. Generally, the Mp (or Mz) of the xylene insoluble fraction can be in a range from any minimum molecular weight to any maximum molecular weight of the xylene insoluble fraction disclosed herein. Therefore, suitable non-limiting ranges for the Mp (or Mz) of the xylene insoluble fraction can include the following ranges: from 150,000 to 750,000, from 200,000 to 900,000, from 200,000 to 750,000, from 200,000 to 600,000, from 200,000 to 500,000, from 250,000 to 1,000,000, from 250,000 to 750,000, from 250,000 to 550,000, from 300,000 to 900,000, from 300,000 to 750,000, from 300,000 to 500,000, or from 325,000 to 650,000 g/mol. Other appropriate ranges for the Mp (or Mz) of the xylene insoluble fraction are readily apparent from this disclosure.

In an embodiment, the xylene insoluble fraction can be characterized by a Mn in a range from 3,800 to 15,000 g/mol. For instance, the Mn of the xylene insoluble fraction can be at least 3,800, 4,000, 4,200, 4,400, or 4,500 g/mol; additionally or alternatively, less than or equal to 15,000, 14,000, 12,000, 10,000, 8,000, 7,500, or 6,500 g/mol. Generally, the Mn of the xylene insoluble fraction can be in a range from any minimum Mn disclosed herein to any maximum Mn of the xylene insoluble fraction disclosed herein. Therefore, suitable non-limiting ranges for the Mn of the xylene insoluble fraction can include the following ranges: from 3,800 to 12,000, from 4,000 to 14,000, from 4,000 to 10,000, from 4,000 to 8,000, from 4,500 to 12,000, from 4,500 to 10,000, or from 4,500 to 7,500 g/mol. Other appropriate ranges for the Mn of the xylene insoluble fraction are readily apparent from this disclosure.

The xylene insoluble fraction, in certain embodiments, also can be characterized by a relatively broad molecular weight distribution, such as by a ratio of Mw/Mn in a range from 5 to 100. For example, in some embodiments, the Mw/Mn of the xylene insoluble fraction can be at least 5, 10, 15, 20, 25, or 30; additionally or alternatively, less than or equal to 100, 90, 80, 70, or 60. Generally, the Mw/Mn of the xylene insoluble fraction can be in a range from any minimum Mw/Mn disclosed herein to any maximum Mw/Mn disclosed herein. Therefore, suitable non-limiting ranges for Mw/Mn of the xylene insoluble fraction can include the following ranges: from 5 to 80, from 5 to 50, from 10 to 100, from 10 to 70, from 20 to 70, from 25 to 100, from 25 to 80, from 25 to 70, from 30 to 90, or from 30 to 60. Other appropriate ranges for the Mw/Mn of the xylene insoluble fraction are readily apparent from this disclosure.

The DSC peak melting temperature of the xylene insoluble fraction typically falls within a range from 105 to 150° C. For instance, the DSC peak melting temperature of the xylene insoluble fraction of the composition can be at least 105, 110, 115, 118, 120, 122, or 124° C.; additionally or alternatively, less than or equal to 150, 145, 140, 136, 134, 132, or 130° C. Generally, the DSC peak melting temperature of the xylene insoluble fraction can be in a range from any minimum peak melting temperature of the xylene insoluble fraction disclosed herein to any maximum peak melting temperature of the xylene insoluble fraction disclosed herein. Therefore, suitable non-limiting ranges for the DSC peak melting temperature of the xylene insoluble fraction of the composition can include the following ranges: from 105 to 150, from 110 to 145, from 110 to 140, from 115 to 134, from 118 to 134, from 120 to 134, from 118 to 132, from 122 to 132, from 122 to 130, from 124 to 136, from 124 to 134, from 124 to 132, or from 124 to 130° C. Other appropriate ranges for the DSC peak melting temperature of the xylene insoluble fraction are readily apparent from this disclosure.

In some embodiments, the polymer compositions can have a zero-shear viscosity at 190° C. in a range from $4.5 \times 10^3$ to $6.5 \times 10^3$, from $4.5 \times 10^3$ to $5.5 \times 10^3$, or from $5.0 \times 10^3$ to $5.5 \times 10^3$ Pa-sec. Additionally or alternatively, the composition can have a Carreau-Yasuda breadth parameter (a CY-a parameter) at 190° C. in a range from 0.5 to 0.75, from 0.55 to 0.7, from 0.55 to 0.65, or from 0.60 to 0.65.

In some embodiments, the compositions disclosed herein can be in the form of polymer pellets. These pellets can be any suitable shape, size, and bulk density, as would be recognized by one of skill in the art, and such as are customarily used in the polyolefin industry. In further embodiments, the composition can comprise one or more suitable additives, non-limiting examples of which can include an antioxidant, an acid scavenger, an antiblock additive, a slip additive, a colorant, a filler, a processing aid, a UV inhibitor or stabilizer, and the like, as well as combinations thereof.

Articles of manufacture can be formed from, and/or can comprise, the compositions (e.g., polymer compositions) of this invention and, accordingly, are encompassed herein. For example, articles which can comprise compositions of this invention can include, but are not limited to, an agricultural film, an automobile part, a bottle, a drum, a fiber or fabric, a food packaging film or container, a food service article, a fuel tank, a geomembrane, a household container, a liner, a molded product, a medical device or material, a pipe, a sheet or tape, a toy, and the like. Various processes can be employed to form these articles. Non-limiting examples of these processes include injection molding, blow molding, rotational molding, film extrusion, sheet extrusion, profile extrusion, thermoforming, and the like. Additionally, additives and modifiers are often added to these compositions in order to provide beneficial polymer processing or end-use product attributes. Such processes and materials are described in *Modern Plastics Encyclopedia*, Mid-November 1995 Issue, Vol. 72, No. 12; and *Film Extrusion Manual-Process, Materials, Properties*, TAPPI Press, 1992; the disclosures of which are incorporated herein by reference in their entirety.

Polymer Composition Recovery Processes

Embodiments of this invention are directed to ethylene oligomerization processes, the production of an oligomer product, and the formation and recovery of a stream comprising a polymer composition, whose typical properties are disclosed herein. One such process can comprise (or consist essentially of, or consist of) (1) contacting ethylene, a catalyst system comprising a transition metal compound and a metal alkyl, and an optional oligomerization diluent in a reactor under oligomerization conditions to form an oligomer product; (2) removing a reactor effluent from the reactor; (3) isolating a heavies stream comprising a liquid fraction and a solid fraction; and (4) removing at least a portion of the liquid fraction from the heavies stream to produce the polymer composition. Another such process can comprise (or consist essentially of, or consist of) (1) contacting ethylene, a catalyst system comprising a transition metal compound and a metal alkyl, and an optional oligomerization diluent in a reactor under oligomerization conditions to form an oligomer product; (2) removing a reactor effluent from the reactor; (3) deactivating the catalyst system (e.g., to produce a deactivated reactor effluent); (4) isolating a heavies stream comprising a liquid fraction and a solid fraction; and (5) removing at least a portion of the liquid fraction from the heavies stream to produce the polymer composition. In an embodiment, the ethylene oligomerization processes can be ethylene trimerization processes; alternatively, ethylene tetramerization processes; or alternatively, ethylene trimerization and tetramerization processes. Generally, the features of the processes (e.g., the catalyst system, the diluent, the oligomerization (trimerization, tetramerization, or trimerization and tetramerization) conditions, methods of deactivating the catalyst system, the materials comprising and/or features of the oligomer (trimerization, tetramerization, or trimerization and tetramerization) product, the materials comprising and/or features of the reactor effluent, the materials comprising and/or features of the polymer composition, the process conditions under which the heavies stream and the polymer composition are formed, among others) are independently described herein, and these features can be combined in any combination to further describe the disclosed processes. Moreover, additional process steps can be performed before, during, or after any of the steps of any of the processes disclosed herein, unless stated otherwise.

In step (1) of the process, ethylene and a catalyst system comprising a transition metal compound and a metal alkyl can be contacted in a reactor under oligomerization (trimerization, tetramerization, or trimerization and tetramerization) conditions to form an oligomer product (trimerization, tetramerization, or trimerization and tetramerization). In some embodiments of this invention, this oligomerization (trimerization, tetramerization, or trimerization and tetramerization) step optionally can be performed in an oligomerization (trimerization, tetramerization, or trimerization and tetramerization) diluent. When employed, any suitable oligomerization (trimerization, tetramerization, or trimerization and tetramerization) diluent can be used.

In embodiment, the oligomerization (trimerization, tetramerization, or trimerization and tetramerization) diluent can be a hydrocarbon or a halogenated hydrocarbon; alternatively, a hydrocarbon; or alternatively, a halogenated hydrocarbon. Hydrocarbons and halogenated hydrocarbon can include, for example, aliphatic hydrocarbons, aromatic hydrocarbons, petroleum distillates, halogenated aliphatic hydrocarbons, halogenated aromatic hydrocarbons, or combinations thereof; alternatively, aliphatic hydrocarbons, aromatic hydrocarbons, halogenated aliphatic hydrocarbons, halogenated aromatic hydrocarbons, and combinations thereof; alternatively, aliphatic hydrocarbons; alternatively, aromatic hydrocarbons; alternatively, halogenated aliphatic hydrocarbons; or alternatively, halogenated aromatic hydrocarbons. Aliphatic hydrocarbons which can be useful as an oligomerization (trimerization, tetramerization, or trimerization and tetramerization) diluent include $C_3$ to $C_{20}$ aliphatic hydrocarbons; alternatively $C_4$ to $C_{15}$ aliphatic hydrocarbons; or alternatively, $C_5$ to $C_{10}$ aliphatic hydrocarbons. The aliphatic hydrocarbons can be cyclic or acyclic and/or can be linear or branched, unless otherwise specified. In some embodiments, the aliphatic hydrocarbon which can be utilized as the oligomerization (trimerization, tetramerization, or trimerization and tetramerization) diluent can be a hydrocarbon olefin (linear or branched, or terminal or internal). Non-limiting examples of suitable acyclic aliphatic hydrocarbon oligomerization (trimerization, tetramerization, or trimerization and tetramerization) diluents that can be utilized singly or in any combination include propane, iso-butane, n-butane, butane (n-butane or a mixture of linear and branched $C_4$ acyclic aliphatic hydrocarbons), pentane (n-pentane or a mixture of linear and branched $C_5$ acyclic aliphatic hydrocarbons), hexane (n-hexane or a mixture of linear and branched $C_6$ acyclic aliphatic hydrocarbons), heptane (n-heptane or a mixture of linear and branched $C_7$ acyclic aliphatic hydrocarbons), octane (n-octane or a mixture of linear and branched $C_8$ acyclic aliphatic hydrocarbons), and combinations thereof; alternatively, iso-butane, n-butane, butane (n-butane or a mixture of linear and branched $C_4$ acyclic aliphatic hydrocarbons), pentane (n-pentane or a mixture of linear and branched $C_5$ acyclic aliphatic hydrocarbons), hexane (n-hexane or a mixture of linear and branched $C_6$ acyclic aliphatic hydrocarbons), heptane (n-heptane or a mixture of linear and branched $C_7$ acyclic aliphatic hydrocarbons), octane (n-octane or a mixture of linear and branched $C_8$ acyclic aliphatic hydrocarbons), and combinations thereof; alternatively, iso-butane, n-butane, butane (n-butane or a mixture of linear and branched $C_4$ acyclic aliphatic hydrocarbons), pentane (n-pentane or a mixture of linear and branched $C_5$ acyclic aliphatic hydrocarbons); alternatively, propane; alternatively, iso-butane; alternatively, n-butane; alternatively, butane (n-butane or a mixture of linear and branched $C_4$ acyclic aliphatic hydrocarbons); alternatively, pentane (n-pentane or a mixture of linear and branched $C_5$ acyclic aliphatic hydrocarbons); alternatively, hexane (n-hexane or a mixture of linear and branched $C_6$ acyclic aliphatic hydrocarbons); alternatively, heptane (n-heptane or a mixture of linear and branched $C_7$ acyclic aliphatic hydrocarbons); or alternatively, octane (n-octane or a mixture of linear and branched $C_8$ acyclic aliphatic hydrocarbons). In other embodiments, the acyclic aliphatic solvent can be a product of the oligomerization (1-hexene and/or 1-octene). Non-limiting examples of suitable cyclic aliphatic hydrocarbon oligomerization (trimerization, tetramerization, or trimerization and tetramerization) diluents include cyclohexane and methyl cyclohexane; alternatively cyclohexane; or alternatively, methylcyclohexane. Aromatic hydrocarbons which can be useful as an oligomerization (trimerization, tetramerization, or trimerization and tetramerization) diluent include $C_6$ to $C_{20}$ aromatic hydrocarbons; or alternatively, $C_6$ to $C_{10}$ aromatic hydrocarbons. Non-limiting examples of suitable aromatic hydrocarbons that can be utilized singly or in any combination include benzene, toluene, xylene (including ortho-xylene, meta-xylene, para-xylene, or mixtures thereof), and ethylbenzene, or combinations thereof; alternatively, benzene; alternatively, toluene; alternatively, xylene (including ortho-xylene, meta-xylene, para-xylene or mixtures thereof); or alternatively, ethylbenzene. Halogenated aliphatic hydrocarbons which can be useful as an oligomerization (trimerization, tetramerization, or trimerization and tetramerization) diluent include $C_1$ to $C_{15}$ halogenated aliphatic hydrocarbons; alternatively, $C_1$ to $C_{10}$ halogenated aliphatic hydrocarbons; or alternatively, $C_1$ to $C_5$ halogenated aliphatic hydrocarbons. The halogenated aliphatic hydrocarbons can be cyclic or acyclic and/or can be linear or branched, unless otherwise specified. Non-limiting examples of suitable halogenated aliphatic hydrocarbons which can be utilized include methylene chloride, chloroform, carbon tetrachloride, dichloroethane, trichloroethane, and combinations thereof; alternatively, methylene chloride, chloroform, dichloroethane, trichloroethane, and combinations thereof; alternatively, methylene chloride; alternatively, chloroform; alternatively, carbon tetrachloride; alternatively, dichloroethane; or alternatively, trichloroethane. Halogenated aromatic hydrocarbons which can be useful as an oligomerization (trimerization, tetramerization, or trimerization and tetramerization) diluent include $C_6$ to $C_{20}$ halogenated aromatic hydrocarbons; or alternatively, $C_6$ to $C_{10}$ halogenated aromatic hydrocarbons. Non-limiting examples of suitable halogenated aromatic hydrocarbons include chlorobenzene, dichlorobenzene, and combinations thereof; alternatively chlorobenzene; or alternatively, dichlorobenzene.

In some embodiments, the reactor effluent can comprise a gaseous fraction, a liquid fraction, and a solid fraction. As used herein, and unless explicitly stated otherwise, the gaseous fraction can include materials which, as pure components, are gasses at standard temperature (25° C.) and pressure (1 atm), the liquid fraction includes materials which, as pure components, are liquids at standard temperature and pressure, and the solid fraction includes materials which, as pure components, are solids at standard temperature and pressure. As one of skill in the art would readily recognize, many of the materials disclosed herein can exist in a different phase when subjected to different processing conditions (e.g., different temperature, different pressure).

The reactor effluent (or deactivated reactor effluent) of this invention often can comprise the following materials: (i) ethylene; (ii) an oligomer product comprising (a) a light oligomer; (b) a specified oligomer that is at least 70 wt. % of the oligomer product, the specified oligomer comprising hexenes, octenes, or a combination thereof; (c) a heavy oligomer; and (d) a polymer; and (iii) the optional oligomerization diluent. The specified oligomer can be at least 70 wt. % of the oligomer product; alternatively, at least 75 wt. %; alternatively, at least 80 wt. %; alternatively, from 70 to 98 wt. %; or alternatively, from 70 to 95 wt. %. The specified oligomer can comprise (or consist essentially of, or consist of) hexenes; alternatively, octenes; or alternatively, hexenes and octenes. For example, in one embodiment, the specified oligomer (or the desired oligomer of ethylene to be produced in the process) can be hexenes (i.e., an ethylene trimerization); then, the light oligomer can comprise butenes, while the heavy oligomer can comprise oligomers from octenes to a molecular weight less than 3400 g/mol. In another embodiment, the specified oligomer (or the desired oligomer of ethylene to be produced in the process) can be octenes (i.e., an ethylene tetramerization); then, the light oligomer can comprise butenes and hexenes, while the heavy oligomer can comprise oligomers from decenes to a molecular weight less than 3400 g/mol. In yet another embodiment, the specified oligomer (or the desired oligomer of ethylene to be produced in the process) can be a mixture of hexenes and octenes (an ethylene trimerization and tetramerization); then, the light oligomer can comprise butenes, while the heavy oligomer can comprise from decenes to a molecular weight less than 3400 g/mol.

Thus, the light oligomer represents ethylene oligomers of lower molecular weight than the specified oligomer, i.e., butenes (if hexenes or hexenes and octenes are the specified oligomers) or butenes and hexenes (if octenes are the specified oligomer). In like manner, the heavy oligomer represents oligomers having a molecular weight greater than the specified oligomer and up to a molecular weight of less than 3400 g/mol. The heavy oligomer can be further subdivided into heavy liquid oligomer and heavy solid oligomer. Heavy liquid oligomer is comprised of the portion of the heavy oligomer compounds which, as a pure component, is a liquid at standard temperature and pressure. Heavy solid oligomer is comprised of the portion of the heavy oligomer compounds which, as a pure component, is a solid at standard temperature and pressure. The polymer is comprised of the portion of the oligomer product compounds having a molecular weight of at least 3400 g/mol.

In the processes described herein, the catalyst system can be deactivated. Deactivating the catalyst system can comprise contacting the reactor effluent with a suitable catalyst system deactivating agent, or subjecting the reactor effluent to suitable process steps to deactivate the catalyst system, or a combination of both. The catalyst system deactivating agent can comprise (or consist essentially of, or consist of) an alcohol compound, an amine compound, or any combination thereof; or alternatively, an alcohol compound. In an embodiment, the alcohol compound can be a monoalcohol compound, a diol compound, a polyol compound, or any combination thereof. In some embodiments, the alcohol compound can comprise, consist essentially of, or consist of, a $C_4$ to $C_{20}$ mono alcohol. In some embodiments, the alcohol compound can comprise, consist essentially of, or consist of, a butanol, a pentanol, a hexanol, a heptanol, an octanol, and nonanol, a decanol, a undecanol, or mixtures thereof. In some embodiments, the alcohol compound can comprise, consist essentially of, or consist of, 1-butanol, 2-butanol, iso-butanol, sec-butanol, t-butanol, 1-hexanol, 2-hexanol, 3-hexanol, 1-heptanol, 2-heptanol, 3-heptanol, 4-heptanol, 1-octanol, 2-octanol, 3-octanol, 4-octanol, 2-ethyl-1-hexanol, 2-methyl-3-heptanol, 1-decanol, 2-decanol, 3-decanol, 4-decanol, 5-decanol, 1-undecanol, 2-udecanol, 7-methyl-2-decanol, a 1-docecanol, a 2-dodecanol, 2-ethyl-1-decanol, and mixtures thereof. In one embodiment, the alcohol compound can comprise, consist essentially of, or consist of, 2-ethyl-1-hexanol.

Additionally or alternatively, the catalyst system can be deactivated by contact with an aqueous solution (e.g., an aqueous Group 1 metal hydroxide solution or an aqueous mineral acid solution). Such deactivation processes to deactivate the catalyst system can also potentially remove a portion, or substantially all, of the metal catalyst system components from the reactor effluent.

In addition to ethylene, the oligomer product (comprising a light oligomer, a specified oligomer comprising hexenes and/or octenes, a heavy oligomer, and a polymer), and the oligomerization diluent (if utilized), the reactor effluent can further comprise catalyst system components. In some embodiments, the reactor effluent can further comprise metal catalyst system components from the catalyst system. Depending upon the process steps utilized (e.g., the catalyst system deactivation step(s) utilized and/or other process steps utilized as described herein), the deactivated reactor effluent can comprise deactivated catalyst system components (e.g., deactivated metal catalyst system components); or alternatively, the deactivated reactor effluent can be substantially devoid of deactivated metal catalyst system components. Herein, a deactivated reactor effluent substantially devoid of metal catalyst system components means that the deactivated reactor effluent can comprise a maximum of 1000, 750, 500, 250, 100, 75, 50, 25, or 10 ppm (by weight) of metal.

In the processes described herein, a heavies stream can be isolated from the reactor effluent (or deactivated reactor effluent), and the heavies stream can comprise a liquid fraction and a solid fraction. In some embodiments, the heavies stream can be isolated by (I) removing at least a portion of a gaseous fraction from the reactor effluent (or the deactivated reactor effluent), (II) removing at least a portion of a liquid fraction from the reactor effluent (or the deactivated reactor effluent), or a combination thereof, using one or more separation steps. In one embodiment, the gaseous fraction can comprise ethylene or, alternatively, ethylene and (gaseous) light oligomer. In another embodiment, the gaseous fraction can comprise the optional (gaseous) oligomerization diluent. In yet another embodiment, the liquid fraction can comprise the optional (liquid) oligomerization diluent; alternatively, liquid oligomer (liquid light oligomer, specified oligomer, and/or heavy liquid oligomer); or alternatively, the optional (liquid) oligomerization diluent, and liquid oligomer (liquid light oligomer, specified oligomer, and/or heavy liquid oligomer). In these and other embodiments, various suitable separations steps can be employed, as would be recognized by those of skill in the art. In an embodiment, the separations steps can include one or more flash processes, distillation processes, and combinations thereof.

In accordance with certain embodiments of this invention, the heavies stream can be isolated by removing (I) at least a portion of the ethylene, (II) at least a portion of the light oligomer, (III) at least a portion of the specified oligomer, (IV) at least a portion of the heavy oligomer, (V) at least a portion of the optional oligomerization diluent, or any combination of (I) to (V), from the reactor effluent (or the deactivated reactor effluent). Suitable separation steps that can be employed include one or more flash processes, distillation processes, and combinations thereof.

Thus, the heavies stream can be isolated from the reactor effluent (or deactivated reactor effluent), and the heavies stream can comprise a liquid fraction and a solid fraction. Additionally, the heavies stream can further comprise metal catalyst system components, deactivated metal catalyst system components, or any combination thereof (e.g., chromium and aluminum species and/or metals). Typically, although not a requirement, the amount of the solid fraction in the heavies stream can fall within a range from 5 to 35 wt. %. For instance, the amount of the solid fraction can be from 5 to 25 wt. %, from 5 to 20 wt. %, from 5 to 15 wt. %, from 10 to 35 wt. %, or from 10 to 25 wt. %, of the heavies stream. This solid fraction of the heavies stream can comprise all or a portion of the heavy solid oligomer, all or a portion of the polymer, or any combination thereof, as well as other materials (e.g., metal catalyst system residues, and/or deactivated catalyst system residues). In an embodiment, the solid fraction can comprise all or a portion of the heavy solid oligomer; alternatively, all of the heavy solid oligomer; or alternatively, a portion of the heavy solid oligomer. In another embodiment, the solid fraction can comprise all or a portion of the polymer; alternatively, all of the polymer; or alternatively, a portion of the polymer. Depending upon the catalyst deactivation agent, upon the process steps utilized (e.g., the catalyst system deactivation step(s) utilized, and/or other process steps utilized as described herein), the solid fraction of the heavies stream can be substantially devoid of deactivated metal catalyst system components. Herein, a solid fraction of the heavies stream substantially devoid of metal catalyst system components means that the solid fraction of the heavies stream can comprise a maximum of 1000, 750, 500, 250, 100, 75, 50, 25, or 10 ppm (by weight) of metal.

The liquid fraction of the heavies stream generally can represent from 65 to 95 wt. % of the heavies stream. Hence, the liquid fraction of the heavies stream can range from 75 to 95 wt. %, from 80 to 95 wt. %, from 85 to 95 wt. %, from 65 to 90 wt. %, or from 75 to 90 wt. %, of the heavies stream. This liquid fraction can comprise all or a portion of the heavy liquid oligomer, all or a portion of the optional oligomerization diluent, or any combination thereof. In an embodiment, the liquid fraction can comprise all or a portion of the heavy liquid oligomer; alternatively, all of the heavy liquid oligomer; or alternatively, a portion of the heavy liquid oligomer. In another embodiment, wherein a liquid oligomerization diluent is utilized, the liquid fraction can comprise all or a portion of the liquid oligomerization diluent; alternatively, a portion of the liquid oligomerization diluent; or alternatively, all of the liquid oligomerization diluent. Moreover, as discussed further herein, the liquid fraction can comprise a portion of the specified oligomer (hexenes and/or octenes) as well as other materials, such as catalyst system or deactivated catalyst system components which are liquids at standard temperature and pressure.

Furthermore, the heavies stream can be characterized by the amount of polymer, heavy oligomer, and oligomerization diluent (when utilized and/or liquid) present in the stream. The polymer can be from 2 to 19 wt. %, from 2 to 18 wt. %, from 2 to 17 wt. %, from 3 to 17 wt. %, from 4 to 16 wt. %, or from 5 to 15 wt. % of the heavies stream. Additionally or alternatively, the heavy oligomer can be from 35 to 80 wt. %, from 35 to 70 wt. %, from 35 to 60 wt. %, from 40 to 80 wt. %, from 40 to 75 wt. %, or from 45 to 70 wt. % of the heavies stream. Additionally or alternatively, the oligomerization diluent (when utilized and/or liquid) can be from 1 to 25 wt. %, from 2 to 25 wt. %, from 2 to 20 wt. %, from 2 to 15 wt. %, from 5 to 25 wt. %, or from 5 to 20 wt. % of the heavies stream. Generally, the heavies stream contains minimal amounts, if any, ethylene, light oligomer, and specified oligomer. For instance, the maximum amount of ethylene in the heavies stream can be 15 wt. %, 10 wt. %, 5 wt. %, 1 wt. %, 0.5 wt. %, or 0.25 wt. %. Further, the maximum amount of the light oligomer in the heavies stream can be 15 wt. %, 10 wt. %, 5 wt. %, 1 wt. %, 0.5 wt. %, or 0.25 wt. %. Similarly, the maximum amount of the specified oligomer in the heavies stream can be 15 wt. %, 12 wt. %, 10 wt. %, 7 wt. %, 5 wt. %, 3 wt. %, or 1 wt. %. In some embodiments, the maximum amount of the total of the ethylene, the light oligomer and the specified oligomer in the heavies stream can be 15 wt. %, 12 wt. %, 10 wt. %, 7 wt. %, 5 wt. %, 3 wt. %, or 1 wt. %.

Consistent with embodiments of this invention, the heavies stream can comprise a liquid fraction and a solid fraction, and in a step consistent with the processes described herein, at least a portion of the liquid fraction can be removed from the heavies stream to produce the polymer composition. Producing the polymer composition by removing at least a portion of the liquid fraction from the heavies stream can be accomplished by using any suitable technique, such as an evaporation process, a distillation process, or combinations thereof. The evaporation and/or distillation process can be conducted at a wide range of suitable temperatures, pressures, and residence times. Evaporation processes, distillation processes, temperatures, pressures, and residence time features are independently disclosed herein and these features can be combined in any combination to further describe the step to produce the polymer composition.

The evaporation and/or distillation process can be conducted at a minimum temperature of 25° C., 50° C., 100° C., 150° C., or 170° C.; additionally or alternatively, at a maximum temperature of 250° C., 230° C., 220° C., 200° C., 190° C., 185° C., 180° C., or 175° C. Generally, the temperature at which the evaporation and/or distillation process can be conducted can be in a range from any minimum temperature disclosed herein to any maximum temperature disclosed herein. Accordingly, suitable non-limiting ranges can include the following: from 50° C. to 250° C., from 100° C. to 230° C., from 150° C. to 230° C., from 170° C. to 230° C., from 150° C. to 220° C., or from 150° C. to 200° C. Other appropriate temperature ranges at which the evaporation and/or distillation process can be conducted are readily apparent from this disclosure.

The evaporation and/or distillation process can be conducted, for instance, at a minimum pressure of 10 mm Hg, 20 mm Hg, 30 mm Hg, 40 mm Hg, or 50 mm Hg; additionally or alternatively, at a maximum pressure of 500 mm Hg, 400 mm Hg, 300 mm Hg, 200 mm Hg, or 150 mm Hg. Generally, the pressure at which the evaporation and/or distillation process can be conducted can be in a range from any minimum pressure disclosed herein to any maximum pressure disclosed herein. Accordingly, suitable non-limiting ranges can include the following: from 10 mm Hg to 500 mm Hg, from 30 mm Hg to 300 mm Hg, from 20 mm Hg to 200 mm Hg, from 40 mm Hg to 400 mm Hg, from 40 mm Hg to 200 mm Hg, or from 50 mm Hg to 150 mm Hg. Other appropriate pressure ranges at which the evaporation and/or distillation process can be conducted are readily apparent from this disclosure.

The residence time of the heavies stream in the evaporation and/or distillation process (e.g., in the evaporation and/or distillation device) can be for a minimum residence time of 1 min, 2 min, 3 min, 5 min, 7 min, or 10 min; additionally or alternatively, for a maximum residence time of 90 min, 75 min, 60 min, 45 min, or 30 min. Generally, the residence time can be in a range from any minimum residence time disclosed herein to any maximum residence time disclosed herein. Accordingly, suitable non-limiting ranges can include the following: from 1 min to 90 min, from 2 min to 60 min, 2 min to 45 min, from 5 min to 60 min, from 5 min to 45 min, from 5 min to 30 min, from 10 min to 75 min, from 10 min to 60 min, from 10 min to 45 min, or from 10 min to 30 min. Other appropriate ranges for the residence time are readily apparent from this disclosure.

In the processes described herein, at least a portion of the liquid fraction can be removed from the heavies stream to produce the polymer composition, and such can be accomplished using an evaporation process and/or distillation process. Suitable devices for performing the evaporation and/or distillation process include, for instance, a thin film evaporator, a wiped film evaporator, or a short-path evaporator, and any combination thereof. A commercial example of one such device is a Filmtruder® evaporator.

As disclosed herein, at least a portion of the liquid fraction can be removed from the heavies stream to produce the polymer composition. In an embodiment, at least a portion of the oligomerization diluent (if utilized and/or liquid) can be removed from the heavies stream to produce the polymer composition. Additionally or alternatively, at least a portion of the heavy oligomer—for example, at least a portion of the heavy liquid oligomer—can be removed from the heavies stream to produce the polymer composition.

The properties and characteristics of the polymer composition that can be formed using these processes are disclosed herein. For instance, the polymer composition can have (a) a high molecular weight hydrocarbon polymer component and a low molecular weight hydrocarbon oligomer component, wherein a ratio of the Mp of the high molecular weight hydrocarbon polymer component to the Mp of the low molecular weight hydrocarbon oligomer component can be in a range from 400:1 to 2000:1; and (b) a liquid component in a range from 1 wt. % to 35 wt. % of the composition, the liquid component comprising saturated hydrocarbon compounds having 16 or less carbon atoms and unsaturated hydrocarbon compounds having 18 or less carbon atoms (or a TGA liquid component in a range from 1 wt. % to 35 wt. % of the composition, or a DSC liquid component in a range from 1 wt. % to 35 wt. % of the composition). Other, aspects, embodiments, and/or features of the composition described herein can be utilized in any combination to further describe the polymer composition produced by the processes described herein.

In additional embodiments, the polymer composition can further comprise metal catalyst system components, deactivated catalyst system components, or any combination thereof, and can have any metal, aluminum, and/or chromium content disclosed herein. Alternatively, the polymer composition can be substantially devoid of metal catalyst system components, deactivated catalyst system components, or any combination thereof, and can thus comprise any maximum of metal, aluminum and chromium, aluminum, or chromium content disclosed herein. Further features of the polymer composition are independently disclosed herein and these independently disclosed polymer composition features can be combined in any combination to further describe the polymer composition.

If desired, metal-containing catalyst system components can be removed at various stages of the process. As an example, prior to removing a portion of the liquid fraction from the heavies stream, at least a portion (e.g., substantially all) of the metal catalyst system components and/or deactivated metal catalyst system components can be removed from the heavies stream. Hence, prior to removing a portion of the liquid fraction from the heavies stream, the heavies stream can be subjected to further process steps comprising (i) contacting the heavies stream with an aqueous solution to form a hydrocarbon/water mixture; and (ii) separating the hydrocarbon/water mixture into (a) an aqueous phase comprising the portion (or substantially all) of the metal catalyst system components and/or deactivated metal catalyst system components, and (b) a hydrocarbon phase comprising hydrocarbon components of the heavies stream.

Additionally or alternatively, metal-containing catalyst system components can be removed at an earlier stage in the process. As an example, prior to isolating the heavies stream, at least a portion (e.g., substantially all) of the metal-containing catalyst system components and/or deactivated metal-containing catalyst system components can be removed from the reactor effluent (or the deactivated reactor effluent). The reactor effluent (or the deactivated reactor effluent) can be subjected to further process steps comprising (i) contacting the reactor effluent (or the deactivated reactor effluent) with an aqueous solution to form an hydrocarbon/water mixture; and (ii) separating the hydrocarbon/water mixture into (a) an aqueous phase comprising the portion (or substantially all) of the metal-containing catalyst system components and/or deactivated metal-containing catalyst system components, and (b) a hydrocarbon phase comprising hydrocarbon components of the reactor effluent (or the deactivated reactor effluent).

Additionally or alternatively, metal-containing catalyst system components can be removed at a later stage in the process. As an example, prior to pelletizing (discussed further hereinbelow), at least a portion (e.g., substantially all) of the metal catalyst system components and/or deactivated metal catalyst system components can be removed from the polymer composition. The polymer composition can be subjected to further process steps comprising (i) contacting the polymer composition with an aqueous solution to form an hydrocarbon/water mixture; and (ii) separating the hydrocarbon/water mixture into (a) an aqueous phase comprising the portion (or substantially all) of the metal catalyst system components and/or deactivated metal catalyst system components, and (b) a hydrocarbon phase comprising hydrocarbon components of the polymer composition.

In these metal removing process steps, the aqueous solution can comprise an aqueous Group I metal hydroxide solution or an aqueous mineral acid solution; alternatively, an aqueous Group I metal hydroxide solution; or alternatively, an aqueous mineral acid solution. Illustrative non-limiting examples of aqueous Group I metal hydroxide solutions include an aqueous sodium hydroxide solution, or an aqueous potassium hydroxide solution; alternatively, an aqueous sodium hydroxide solution; or alternatively, an aqueous potassium hydroxide solution. Illustrative non-limiting examples of aqueous mineral acid solutions include aqueous hydrochloric acid solutions, aqueous hydrobromic acid solutions, aqueous nitric acid solutions, aqueous nitrous acid solutions, aqueous sulfuric acid solutions, aqueous sulfurous acid solutions, aqueous phosphoric acid solutions, or aqueous phosphorous acid solutions; alternatively, aqueous hydrochloric acid solutions, aqueous hydrobromic acid solutions, aqueous phosphoric acid solutions, aqueous sulfuric acid solutions, or aqueous nitric acid solutions. Generally, the amount of the aqueous Group I metal hydroxide solution and the concentration of Group I metal hydroxide in the aqueous Group I metal hydroxide solution or the amount of the aqueous mineral acid solution and concentration of the mineral acid in the an aqueous mineral acid solution utilized can be any amount or concentration which effectively removes the desired amount of the metal components from the stream being processed. The aqueous solutions can further comprise additional compounds which can prove advantageous for the process (e.g. emulsion breaking agents, corrosion inhibitors, etc.). Also, as it pertains to these metal removing process steps, the steps can further comprise drying the hydrocarbon phase by any suitable means. In an embodiment, the hydrocarbon phase can be dried by passing the hydrocarbon phase through a water absorbent. Non-limiting examples include aluminum oxide, molecular sieves (e.g., 3A, 4A, and/or 5A), silica gel, magnesium oxide, or any combination thereof. The dried hydrocarbon phase resulting from the heavies stream (or from the reactor effluent, or from the deactivated reactor effluent, or from the polymer composition, or any other aqueous solution process stream) can then be further processed as described herein.

The metal removing process steps can be effective at reducing the amount of metal catalyst system or deactivated metal catalyst system components or residues. For instance, the hydrocarbon phase can be substantially devoid of metal, chromium, aluminum, or chromium and aluminum. Within this application and claims, the hydrocarbon phase substantially devoid of metal, aluminum and chromium, aluminum, or chromium means that the composition can have a maximum metal, aluminum and chromium, aluminum, or chromium content of 1000, 750, 500, 250, 100, 75, 50, 25, or 10 ppm (by weight).

In particular embodiments of this invention, the process can further comprise a step of forming polymer pellets from the polymer composition. The step of forming polymer pellets can comprise processing the polymer composition through a pelletizing die (non-limiting examples include strand, underwater, water ring, etc.) using any suitable apparatus. For instance, an extruder, a single screw extruder, a twin screw extruder, a gear pump, or other suitable apparatus can be used.

Various additives can be incorporated to provide beneficial processing and/or end-use attributes. Accordingly, the step of forming pellets can comprise contacting the polymer composition with any suitable additive, such as an antioxidant, an acid scavenger, an antiblock additive, a slip additive, a colorant, a filler, a polymer processing aid, a UV inhibitor or stabilizer, and the like, as well as combinations thereof, and processing the polymer composition and additive(s) through a pelletizing die to form polymer pellets containing the additive(s). As above, suitable extrusion and/or gear pump apparatus can be used.

This invention also encompasses methods of preparing articles of manufacture from the polymer pellets resulting from the polymer composition. One such method for preparing an article of manufacture can comprise forming the article from the polymer pellets via any suitable technique, such as melt processing, extruding, molding, thermoforming, etc., and including combinations thereof.

Referring now to the drawings, FIG. 1 illustrates an embodiment of a process 100 consistent with the present invention. A reactor effluent 25 can exit a reactor 20 and enter a first separation device 30. The first separation device 30 can be, for example, a distillation column (or alternatively, a flash drum), although not limited thereto. Optionally, prior to entering the first separation device 30, the reactor effluent 25 can be fed to a flash drum (not shown), and the top and bottom exits from the flash drum can be fed to appropriate locations in the first separation device 30, or to other device(s) or location(s) within the process. After exiting the reactor 20, the reactor effluent 25 can be contacted with a first catalyst system deactivation agent 28, if desired. Optionally, the intersection of 28 with 25 can represent the point at which the catalyst system can be deactivated using the processes described herein that comprise contacting the reactor effluent with an aqueous solution.

A light stream 32 from the first separation device 30 generally can contain predominantly lighter, lower molecular weight materials, such as ethylene, the light oligomer, the specified oligomer (e.g., hexenes and/or octenes), and oligomerization diluent, if used and/or has properties such that is present at this stage of the process. A heavies stream 35 can exit the bottom of the first separation device 30 and enter an evaporator 40. The typical components present in the heavies stream 35 are described herein, e.g., the predominant components of the heavies stream 35 often can be heavy oligomer, polymer, catalyst residue (or deactivated catalyst residue), and oligomerization diluent, if used and/or has properties such that is present at this stage of the process. The evaporator 40 can be, for example, a thin film evaporator, a wiped film evaporator, or a short-path evaporator. Optionally, prior to entering the evaporator 40, the heavies stream 35 can be fed to a flash drum (not shown), and the top and bottom exits from the flash drum can be fed to appropriate locations in the evaporator 40, or to other device(s) or location(s) within the process. After exiting the first separation device 30, the heavies stream 35 can be contacted with a second catalyst system deactivation agent 38, if desired. Optionally, the intersection of 38 with 35 can represent the point at which at least a portion of the metal catalyst system components (or deactivated metal catalyst system components) can be removed using the processes described herein that comprise contacting the stream with an aqueous solution.

A top exit stream 42 from the evaporator 40 generally can contain predominantly heavy liquid oligomer and oligomerization diluent (if used and/or has properties such that is present at this stage of the process), while a polymer composition stream 45 can exit the bottom of the evaporator 40. Optionally, the polymer composition stream 45 can be contacted with a third catalyst system deactivation agent 48, if desired, or the intersection of 45 with 48 can represent the point at which at least a portion of the metal catalyst system components (or deactivated metal catalyst system components) can be removed using the processes described herein that comprise contacting the stream with an aqueous solution. Subsequently, the polymer composition stream 45 can be fed to a melt processing operation, e.g., including an extruder or gear pump, and formed into pellets via a suitable pelletizing die (not shown).

The elements and streams shown in process 200 of FIG. 2 are generally as described for FIG. 1, with the following exceptions. A desired product stream 37 can exit the first separation device 30 between a light stream 33 and the heavies stream 35, and the desired product stream 37 can contain predominantly the specified oligomer (e.g., hexenes and/or octenes) and oligomerization diluent (if used and/or has properties such that is present at this stage of the process). In FIG. 2, the light stream 33 generally can contain ethylene and the light oligomer.

Figure 3:
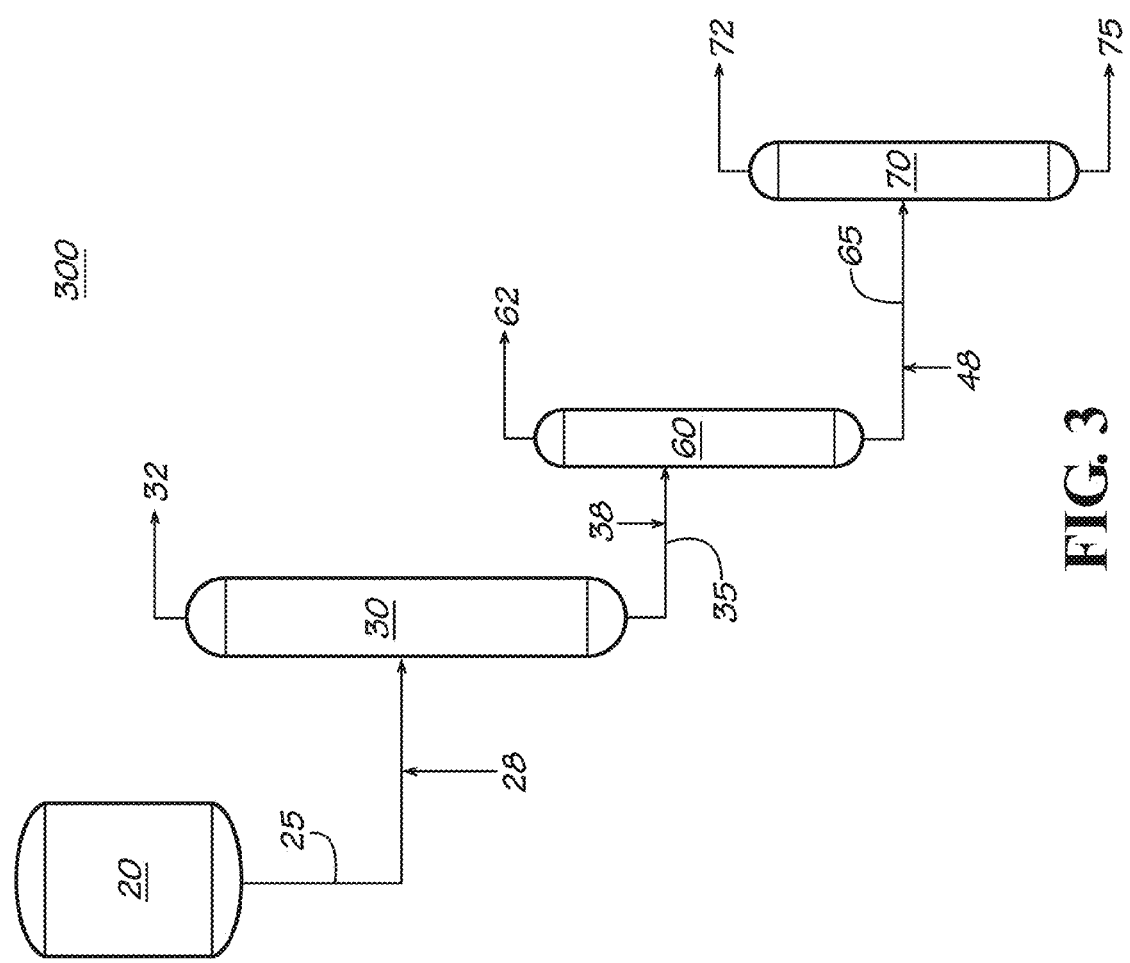
FIG. 3 presents a schematic diagram of a process in yet another embodiment of the present invention.

In process 300 of FIG. 3, the reactor 20, reactor effluent 25, first catalyst system deactivating agent 28, first separation device 30, light stream 32, second catalyst system deactivation agent 38, third catalyst system deactivation agent 48, and optional flash drums are generally as described for FIG. 1. However, in FIG. 3, a bottoms stream 35 can enter a second separation device 60, which can be, for example, a distillation column, although not limited thereto. Optionally, prior to entering the evaporator 60, the bottoms stream 35 can be fed to a flash drum (not shown), and the top and bottom exits from the flash drum can be fed to appropriate locations in the evaporator 60, or to other device(s) or location(s) within the process. An overhead stream 62 from the second separation device 60 generally can contain predominantly the specified oligomer (e.g., hexenes and/or octenes) and oligomerization diluent (if used and/or has properties such that is present at this stage of the process). A heavies stream 65 can exit the bottom of the second separation device 60 and enter an evaporator 70. Optionally, prior to entering the evaporator 70, the heavies stream 65 can be fed to a flash drum (not shown), and the top and bottom exits from the flash drum can be fed to appropriate locations in the evaporator 70, or to other device(s) or location(s) within the process. The evaporator 70 can be, for example, a thin film evaporator, a wiped film evaporator, or a short-path evaporator.

A top exit stream 72 from the evaporator 70 generally can contain predominantly heavy liquid oligomer and oligomerization diluent (if used and/or has properties such that is present at this stage of the process), while a polymer composition stream 75 can exit the bottom of the evaporator 70. As above, the polymer composition stream 75 can be fed to a melt processing operation and formed into pellets via a pelletizing die. Optionally, prior to melt processing into pellets, the polymer composition stream 75 can be subjected to an aqueous solution wash to remove at least a portion of the metal catalyst system components (or deactivated metal catalyst system components) from the polymer composition.

Catalyst Systems

In step (1) of the processes disclosed herein, ethylene can be contacted with a catalyst system comprising a transition metal compound and a metal alkyl, as well as an optional oligomerization diluent, in a reactor under oligomerization conditions to form an oligomer product. Any catalyst system suitable for the oligomerization (trimerization, tetramerization, or trimerization and tetramerization) of ethylene can be employed. In one embodiment, for example, the transition metal compound can comprise (or consist essentially, or consist of) a chromium compound, and the metal alkyl can comprise (or consist essentially, or consist of) an alkylaluminum compound.

In an embodiment, the catalyst system can comprise a chromium compound, an amine, amide, or imide compound, a metal alkyl compound, and optionally, a halide containing compound. In some embodiments, the catalyst system can comprise a chromium compound, a pyrrole compound, a metal alkyl compound, and optionally, a halide containing compound. The catalyst system using a pyrrole compound can be referred to as a chromium-pyrrole catalyst system. The chromium-pyrrole catalyst system can be an ethylene trimerization catalyst system where the specified oligomer typically comprises at least 70 wt. % hexenes. In some chromium-pyrrole catalyst system embodiments, the chromium compound can comprise, or consist essentially of, a chromium carboxylate and the alkyl aluminum compound can comprise, or consist essentially of, a trialkylaluminum compound, a dialkylaluminum halide, an alkylaluminum dihalide, an alkylaluminum sesquihalide, or any combination thereof. In some chromium-pyrrole catalyst system embodiments, the optional halide containing compound can be an organo halide compound, a metal halide compound (e.g., an inorganic metal halide compound or an alkyl metal halide compound), or a combination thereof. In a chromium-pyrrole catalyst system embodiment, this catalyst system can comprise chromium (III) 2-ethylhexanoate, 2,5-dimethyl pyrrole, triethylaluminum, and diethylaluminum chloride. Additional information regarding the use of chromium-pyrrole catalyst systems for oligomerizing ethylene (including specific examples) can be found in, but not limited to, U.S. Pat. No. 5,198,563, U.S. Pat. No. 5,288,823, EP 608447A1, U.S. Pat. No. 5,331,104, U.S. Pat. No. 5,340,785, U.S. Pat. No. 5,360,879, U.S. Pat. No. 5,376,612, U.S. Pat. No. 5,382,738, U.S. Pat. No. 5,399,539, U.S. Pat. No. 5,438,027, U.S. Pat. No. 5,470,926, U.S. Pat. No. 5,543,375, U.S. Pat. No. 5,523,507, U.S. Pat. No. 5,563,312, EP 706983A1, U.S. Pat. No. 5,689,028, U.S. Pat. No. 5,750,816, U.S. Pat. No. 5,763,723, U.S. Pat. No. 5,814,575, U.S. Pat. No. 5,856,257, U.S. Pat. No. 5,856,612, U.S. Pat. No. 5,859,303, U.S. Pat. No. 5,910,619, U.S. Pat. No. 6,133,495, U.S. Pat. No. 6,380,451, U.S. Pat. No. 6,455,648, U.S. Pat. No. 7,157,612, U.S. Pat. No. 7,384,886, U.S. Pat. No. 7,476,775, U.S. Pat. No. 7,718,838, U.S. Pat. No. 7,820,581, U.S. Pat. No. 7,910,670, U.S. Pat. No. 8,049,052, U.S. Pat. No. 8,329,608, U.S. Pat. No. 8,344,198, U.S. Pat. No. 8,471,085, US 2010/0036185, US 2010/0113257, US 2010/0113851, US 2010/0113852, US 2013/0150605, US 2010/0331503, or US 2013/0150642.

In an embodiment, the catalyst system can comprise a chromium compound, a diphosphinoaminyl compound, and a metal alkyl compound. In another embodiment, the catalyst system can comprise a chromium complex of a diphosphinoaminyl compound, and a metal alkyl compound. These catalyst systems can be generically referred to as chromium-PNP catalyst systems. Depending upon the diphosphinoaminyl compound, the chromium-PNP catalyst systems can be an ethylene tetramerization catalyst system where the specified oligomer comprises at least 70 wt. % octenes or a trimerization and tetramerization catalyst system where the specified oligomer comprises at least 70 wt. % hexenes and octenes. In some chromium-PNP catalyst system embodiments, the chromium compound of the catalyst system or the chromium compound of the chromium complex of a diphosphinoaminyl compound, can comprise, or consist essentially of, a chromium halide, carboxylate, β-diketonate, hydrocarboxide, nitrate, sulfate, phosphate, or chlorate; alternatively, a chromium halide, carboxylate, or acetonate; alternatively, a chromium halide; alternatively, a chromium carboxylate; or alternatively, chromium β-diketonate. In some chromium-PNP catalyst system embodiments, the alkyl aluminum compound can comprise, or consist essentially of, a trialkylaluminum compound, an alkylaluminum halide (e.g., a dialkylaluminum halide, an alkylaluminum dihalide, and/or an alkylaluminum sesquihalide), an aluminoxane, or combinations thereof; or alternatively, comprises an alumoxane. Additional information regarding the use of chromium-PNP catalyst systems for oligomerizing ethylene (including specific examples) can be found in, but not limited to, U.S. Pat. No. 7,285,607, U.S. Pat. No. 7,297,832, U.S. Pat. No. 7,323,524, U.S. Pat. No. 7,323,524, U.S. Pat. No. 7,378,537, U.S. Pat. No. 7,511,183, U.S. Pat. No. 7,525,009, U.S. Pat. No. 7,829,749, U.S. Pat. No. 7,906,681, U.S. Pat. No. 7,964,763, U.S. Pat. No. 7,994,363, U.S. Pat. No. 8,076,523, U.S. Pat. No. 8,134,038, U.S. Pat. No. 8,252,956, U.S. Pat. No. 8,252,955, U.S. Pat. No. 8,268,941, U.S. Pat. No. 8,334,420, U.S. Pat. No. 8,367,786, U.S. Pat. No. 8,461,406, US 2009/0306442, US 2011/0257350, US 2011/0282016, US 2012/0041241, US 2012/0088933, US2012/0101321, US 2012/0142989, US 2012/0199467, US 2012/0271087, US 2012/0316303, and WO 2013013300.

In another embodiment, the catalyst system can comprise a chromium compound, an $N^2$-phosphinylamidine compound, and a metal alkyl compound. In another embodiment, the catalyst system can comprise a chromium complex of an $N^2$-phosphinylamidine compound, and a metal alkyl compound. These catalyst systems can be generically referred to as chromium-$N^2$-phosphinylamidine catalyst systems.

Depending upon the $N^2$-phosphinylamidine compound, these catalyst systems can be an ethylene trimerization catalyst system where the specified oligomer comprises at least 70 wt. % hexenes or a trimerization and tetramerization catalyst system where the specified oligomer comprises at least 70 wt. % hexenes and octenes. In some chromium-$N^2$-phosphinylamidine catalyst system embodiments, the chromium compound of the catalyst system or the chromium compound of the chromium complex of a $N^2$-phosphinylamidine compound, can comprise, or consist essentially of, a chromium halide, carboxylate, β-diketonate, hydrocarboxide, nitrate, or chlorate; alternatively, a chromium halide, carboxylate, hydrocarboxide, or acetonate; alternatively, a chromium halide; alternatively, a chromium carboxylate; alternatively, a chromium hydrocarboxide; or alternatively, chromium β-diketonate. In some chromium-$N^2$-phosphinylamidine catalyst system embodiments, the alkyl aluminum compound can comprise, or consist essentially of, a trialkylaluminum compound, an alkylaluminum halide (e.g., a dialkylaluminum halide, an alkylaluminum dihalide, and/or an alkylaluminum sesquihalide), an alkylaluminum alkoxide, an aluminoxane, or combinations thereof; or alternatively, comprises an alumoxane. Additional information regarding the use of chromium-$N^2$-phosphinylamidine catalyst systems for oligomerizing ethylene (including specific examples) can be found in, but not limited to, U.S. Pat. No. 8,680,003.

In another embodiment, the catalyst system can comprise a chromium compound, an $N^2$-phosphinylformamidine compound, and a metal alkyl compound. In another embodiment, the catalyst system can comprise a chromium complex of an $N^2$-phosphinylformamidine compound, and a metal alkyl compound. These catalyst systems can be generically referred to as chromium compound-$N^2$-phosphinylformamidine catalyst systems. Depending upon the $N^2$-phosphinylformamidine compound, these catalyst systems can be an ethylene trimerization catalyst system where the specified oligomer comprises at least 70 wt. % hexenes or a trimerization and tetramerization catalyst system where the specified oligomer comprises at least 70 wt. % hexenes and octenes. In some chromium-$N^2$-phosphinylforamidine catalyst system embodiments, the chromium compound of the catalyst system or the chromium compound of the chromium complex of a $N^2$-phosphinylforamidine compound, can comprise, or consist essentially of, a chromium halide, carboxylate, β-diketonate, hydrocarboxide, nitrate, or chlorate; alternatively, a chromium halide, carboxylate, hydrocarboxide, or acetonate; alternatively, a chromium halide; alternatively, a chromium carboxylate; alternatively, a chromium hydrocarboxide; or alternatively, chromium β-diketonate. In some chromium-$N^2$-phosphinylforamidine catalyst system embodiments, the alkyl aluminum compound can comprise, or consist essentially of, a trialkylaluminum compound, an alkylaluminum halide (e.g., a dialkylaluminum halide, an alkylaluminum dihalide, and/or an alkylaluminum sesquihalide), an alkylaluminum alkoxide, an aluminoxane, or combinations thereof; or alternatively, comprises an alumoxane. Additional information regarding the use of the chromium compound-$N^2$-phosphinylformamidine catalyst systems for oligomerizing ethylene (including specific examples) can be found in, but not necessarily limited to, PCT patent application PCT/US13/75936.

In yet another embodiment, the catalyst system can comprise a chromium compound, an $N^2$-phosphinylguanidine compound, and a metal alkyl compound. In still another embodiment, the catalyst system can comprise a chromium complex of an $N^2$-phosphinylguanidine compound, and a metal alkyl compound. These catalyst systems can be generically referred to as chromium compound-$N^2$-phosphinylguanidine catalyst systems. Depending upon the $N^2$-phosphinyl guanidine compound, these catalyst systems can be an ethylene trimerization catalyst system where the specified oligomer comprises at least 70 wt. % hexenes or a trimerization and tetramerization catalyst system where the specified oligomer comprises at least 70 wt. % hexenes and octenes. In some chromium-$N^2$-phosphinylguanidine catalyst system embodiments, the chromium compound of the catalyst system or the chromium compound of the chromium complex of a $N^2$-phosphinylguanidine compound, can comprise, consist essentially of, a chromium halide, carboxylate, β-diketonate, hydrocarboxide, nitrate, or chlorate; alternatively, a chromium halide, carboxylate, hydrocarboxide, or acetonate; alternatively, a chromium halide; alternatively, a chromium carboxylate; alternatively, a chromium hydrocarboxide; or alternatively, chromium β-diketonate. In some chromium-$N^2$-phosphinylguanidine catalyst system embodiments, the alkyl aluminum compound can comprise, or consist essentially of, a trialkylaluminum compound, an alkylaluminum halide (e.g., a dialkylaluminum halide, an alkylaluminum dihalide, and/or an alkylaluminum sesquihalide), an alkylaluminum alkoxide, an aluminoxane, or combinations thereof; or alternatively, comprises an alumoxane. Additional information regarding the use of chromium compound-$N^2$-phosphinylguanidine catalyst systems for oligomerizing ethylene (including specific examples) can be found in, but not necessarily limited to, US 2013/0331629.

Combinations of more than one catalyst systems described herein can be employed, if desired. Moreover, the processes disclosed herein are not limited solely to the catalyst systems provided hereinabove.

EXAMPLES

The invention is further illustrated by the following examples, which are not to be construed in any way as imposing limitations to the scope of this invention. Various other aspects, embodiments, modifications, and equivalents thereof which, after reading the description herein, may suggest themselves to one of ordinary skill in the art without departing from the spirit of the present invention or the scope of the appended claims.

Polymer density was determined in grams per cubic centimeter (g/cm$^3$) on a compression molded sample, cooled at about 15° C. per hour, and conditioned for about 40 hours at room temperature in accordance with ASTM D1505-10 and ASTM D4703-10a.

Molecular weights and molecular weight distributions were obtained using a PL-GPC 220 (Polymer Labs, an Agilent Company) system equipped with a IR4 detector (Polymer Char, Spain) and three Styragel® HMW-6E GPC columns (Waters, Mass.) running at 145° C. The flow rate of the mobile phase 1,2,4-trichlorobenzene (TCB) containing 0.5 g/L 2,6-di-t-butyl-4-methylphenol (BHT) was set at 1 mL/min, and polymer solution concentrations were in the range of 1.0-1.5 mg/mL, depending on the molecular weight. Sample preparation of the polymer composition was conducted at 150° C. for nominally 4 hr with occasional and gentle agitation, before the solutions were transferred to sample vials for injection. An injection volume of about 200 μL was used. The integral calibration method was used to deduce molecular weights and molecular weight distributions using a Chevron Phillips Chemicals Company's HDPE polyethylene resin, MARLEX® BHB5003, as the broad standard. Calibration samples of MARLEX® BHB5003 can be obtained from Chevron Phillips Chemicals Company, LP. Mn is the number-average molecular weight, Mw is the weight-average molecular weight, Mz is the z-average molecular weight, and Mp is the peak molecular weight.

TGA measurement performed on a Q500 TGA (Thermal Analysis Instruments). A 10 to 20 mg sample was placed in a platinum pan and loaded onto the microbalance inside the TGA furnace. The sample was initially equilibrated at 30° C. with a $N_2$ flow rate of 60 ml/min and then heated to 105° C. at a temperature rate of 1° C./min. The sample was then held at 105° C. for 2 minutes. After the 2 minute hold period, $N_2$ flow was switched to an air flow at 60 ml/min) and the sample heated to 600° C. at a temperature rate of 10° C./min. The sample was held at the maximum temperature for 120 min before cooling down to 30° C. at 10° C./min. Weight loss was recorded during the process. The amount of the TGA liquid component of the composition is the amount of weight lost (calculated on the basis of the entire composition) from the composition (or from the xylene soluble fraction of the composition) from 0° C. to 240° C.

Vacuum oven liquids test was perform as follows. A weighed sample of the composition was placed in an aluminum pan or tray. The tray was then placed in a vacuum oven operating at approximately 150° C. and 22 mm Hg for at least 12 hours or longer until there was no significant weight change between successive sample weights taken at 1 hour intervals. The vacuum oven liquids content was then determined as the amount of material lost during the test.

The xylene extraction method used to form a xylene soluble fraction and a xylene insoluble fraction of the polymer composition was performed as follows. A 1-liter flask containing approximately 15 g of the polymer composition sample and 400 mL of xylene was placed in an oven at approximately 125° C. The flask was shaken to thoroughly mix the contents every 30 min. After 5 hr, the flask—containing a brown solution with insoluble material—was removed from the oven and cooled in ambient air for 12 hr. Subsequently, the xylene insoluble fraction in the flask was filtered off, collected, and dried in a vacuum oven operating at a pressure of approximately 50 torr and a temperature of 80° C. until no additional weight loss was observed (typically about 1 hour). The xylene soluble fraction was collected and dried in a vacuum oven after the xylene solvent was removed by a rotor evaporator run at a pressure of 30 to 40 mbar and a bath temperature of about 80° C. for about 1 hour.

Differential Scanning calorimeter (DSC) testing was performed as follows. A 5-8 mg sample was prepared and sealed in a Tzero® aluminum pan with lid, then placed in a DSC instrument, TA Instruments Model Q2000 DSC. The sample was tested inside a heating cell with a constant nitrogen blanket flow of 50 mL/min and the following program method:
1: External event: On
2: Equilibrate at 0° C.
3: Data storage: On
4: Ramp 20° C./min to 180° C. ($1^{st}$ heat)
5: Mark end of $1^{st}$ heat
6: Isothermal for 5 min
7: Ramp 20° C./min to 0° C. (cooling cycle)
8: Mark end of cooling cycle
9: Isothermal for 5 min
10: Ramp 20° C./min to 180° C. ($2^{nd}$ heat)
11: Mark end of $2^{nd}$ heat
12: Data storage: Off
13: Equilibrate at 30° C.
14: End of method
Data reported herein based upon DSC tests are based upon the $2^{nd}$ heat scan.

The Gas Chromatograph/Mass Spectrometer (GC/MS) apparatus included a ThermoFinnigan TSQ 7000 triple quad mass spectrometer directly interfaced to a Varian 3800 GC; the GC column was a J&W DB-5 (95% methyl/5% phenyl polysiloxane) 30 m×0.25 mm×0.25 μm film thickness. The temperature program was a 40° C. hold temperature for 1 min, then a 5° C./min ramp to 300° C., then a hold at this temperature for 2 min. The carrier gas was helium, at 1.3 mL/min constant flow. The injector was set at 300° C., 40:1 split, and 0.2 μL injection volume. The interface was deactivated fused silica tubing set at 290° C. The mass spectrometer was in single quad mode, 70 ev EI, 35 to 350 scan range, and 2 scans/sec. Compound identification was based on a combination of NIST (National Institute of Standards and Technology) library spectra plus retention index matching with a proprietary database.

The xylene soluble fraction sample for GC/MS testing was dissolved in 70° C. toluene and injected into the instrument set at the conditions listed above. At each carbon number present in the sample, compounds were grouped into these 4 types: branched/internal olefins, diolefins, l-ene, and n-paraffin. Chromatographic peaks corresponding to the 4 compound types were grouped and the areas entered into an Excel spreadsheet. Raw GC/MS areas for each type were normalized against equivalent results obtained using GC with flame ionization detection and in the end, normalized to 100% using the GC-FID as the definitive data. The average molecular weight of the sample was calculated using the chromatographic results multiplied by the corresponding molecular weight of each compound.

GC-FID analysis was performed on an Agilent® 6890 gas chromatograph using a Restek RTX-1 30 m×280 μm×0.50 μm capillary column with Flame Ionization Detector using helium as the carrier gas. The sample was dissolved in isooctane at a concentration of about 10 mg/mL and injected (1.0 μL) into a split/splitless PVT inlet. The inlet parameters were an inlet temperature of 330° C., an inlet pressure of 11.7 psi, an inlet total flow of 83.9 mL/minute, and an inlet split ratio of 50:1. The temperature program for the GC-FID analysis was an initial temperature of 40° C. for 10 minutes, followed by a temperature ramp of 15° C./minute to 330° C., and a temperature hold at 330° C. for 30 minutes. The GC-FID detector was operated at a temperature of 330° C. having a hydrogen gas flow of 35.0 mL/minute, an air flow of 400 mL/minute, and a makeup helium gas flow of 2.0 mL/minute. GC-FID analysis data was acquired with Agilent Chemstation®.

Metals analysis was performed on the polymer composition using Inductively Coupled Plasma Atomic Emission Spectrometry (ICP-AES). First, approximately 0.25 grams of the sample were weighed into a 50-mL quartz vessel, then 3.5 grams of concentrated nitric acid were added. The vessel was sealed and placed into an Anton Paar high pressure asher, where the mixture was heated at 300° C. under 1500 psig of nitrogen gas for 3 hr. The resulting solution was diluted with 10% nitric acid/90% deionized water until a dilution factor of approximately 100 was reached. Solutions could be further diluted to analyze for elements that were outside of the ICP-AES instrument's calibration range. A Spectro Arcos inductively coupled plasma atomic emission spectrometer was calibrated in a 10% nitric acid/90% deionized water matrix with the following analyte concentrations: blank, 0.25 ppm, 0.50 ppm, 1 ppm, 5 ppm, and 10 ppm. Digested samples were pre-diluted in a 10% nitric acid/90% deionized water to match the calibration matrix and analyzed for various elements, including chromium and aluminum. Samples were analyzed in triplicate, with reported results being the average of the three measurements. Quality control for this procedure included an initial standardization consisting of a blank and 5 ppm standard, as well as the analysis of 0.25 ppm and 1 ppm check standards; 1 ppm check standards were monitored after every seven samples.

Ash values were determined by placing a 5 g sample in a clean, dry, and pre-weighed crucible and then heating the sample at 815° C. for 15 minutes using a Barnstead Thermoline 47900 muffle furnaces with Eurotherm 2116 controllers. An Oak River Technology 0400-3209 robotic system for used for crucible handling. The sample was then cooled using compressed air for 10 minutes. The crucible was then weighed and weight percent ash calculated.

Example 1

To illustrate the processes described herein, a stream containing a liquid fraction and a solid fraction was obtained from a commercial ethylene trimerization process. The commercial trimerization process utilized a chromium-pyrrole catalyst system as described herein to produce a reactor effluent. The reactor effluent was then deactivated using an alcohol deactivating agent, and processed through a series of flash drums and/or distillation columns to isolate the stream comprising a liquid fraction and a solid fraction by removing (a) a majority of the unreacted ethylene, light oligomer product, and hexene product, and (b) a portion of the heavy oligomer product and a portion of the oligomerization diluent. The chromium-pyrrole catalyst system, the ethylene trimerization process conditions, the trimerization reactor effluent, the trimerization reactor effluent deactivation, and the flash and/or distillation process utilized to produce the stream containing a liquid fraction and a solid fraction are described in one or more of EP 608447A1, U.S. Pat. No. 5,543,375, U.S. Pat. No. 5,563,312, EP 706983A1, U.S. Pat. No. 5,689,028, U.S. Pat. No. 5,750,816, U.S. Pat. No. 5,856,257, U.S. Pat. No. 5,856,612, U.S. Pat. No. 5,859,303, U.S. Pat. No. 5,910,619, U.S. Pat. No. 6,133,495, U.S. Pat. No. 6,380,451, U.S. Pat. No. 6,455,648, U.S. Pat. No. 7,157,612, U.S. Pat. No. 7,384,886, U.S. Pat. No. 7,476,775, U.S. Pat. No. 7,718,838, U.S. Pat. No. 7,820,581, U.S. Pat. No. 7,910,670, U.S. Pat. No. 8,049,052, U.S. Pat. No. 8,329,608, U.S. Pat. No. 8,344,198, U.S. Pat. No. 8,471,085, US 2010/0036185, US 2010/0113257, US 2010/0113851, US 2010/0113852, US 2013/0150605, US 2010/0331503, or US 2013/0150642. The stream containing a liquid fraction and a solid fraction was stored in and shipped to a further processing site in intermediate bulk containers (hereafter IBCs). Analysis of the IBCs at the processing site indicated that the IBCs contained from 7 wt. % to 10 wt. % solids.

For the experiments, the stream containing the liquid fraction and a solid fraction was split into two separate streams. Each stream was then processed through a 5.4 ft² LCI Filmtruder™ Thin Film Evaporator System (hereafter LCI Filmtruder™ System) equipped with either an S-bearing or a pin and journal bushing. These tests were performed with an approximate 1 mm film thickness. The table below provides the operating ranges utilized to produce a polymer composition from the stream process through the LCI Filmtruder System.

| Operating Parameter | S Bearing Test | | Pin and Journal Test | |
| --- | --- | --- | --- | --- |
| | Minimum Value | Maximum Value | Minimum Value | Maximum Value |
| Feed Rate, lbs/hour | 50 | 65 | 145 | 175 |
| Vacuum, mm Hg | 120 | 135 | 145 | 185 |
| Rotor Speed, rpm | 490 | 550 | 690 | 925 |
| Feed Temperature, ° C. | 140 | 145 | 160 | 165 |
| Distillate Temperature, ° C. | 130 | 135 | 129 | 135 |
| Bottoms Temperature, ° C. | 135 | 165 | 180 | 195 |
| Distillate Rate, lbs/hour | 40 | 60 | 145 | 175 |
| Bottoms Rate, lbs/hour | 6.5 | 8 | 21 | 24 |
| Distillation Ratio | 84 | 90 | 84 | 88 |

During the runs, a valve directed the flow from a gear pump at the bottom of the LCI Filmtruder System to either a composite sample container or through a Gala underwater pelletizer equipped with a 3.5 inch cutter and a centrifugal pellet dryer. Samples from the LCI Filmtruder System test were then subjected to analysis.

Figure 4:
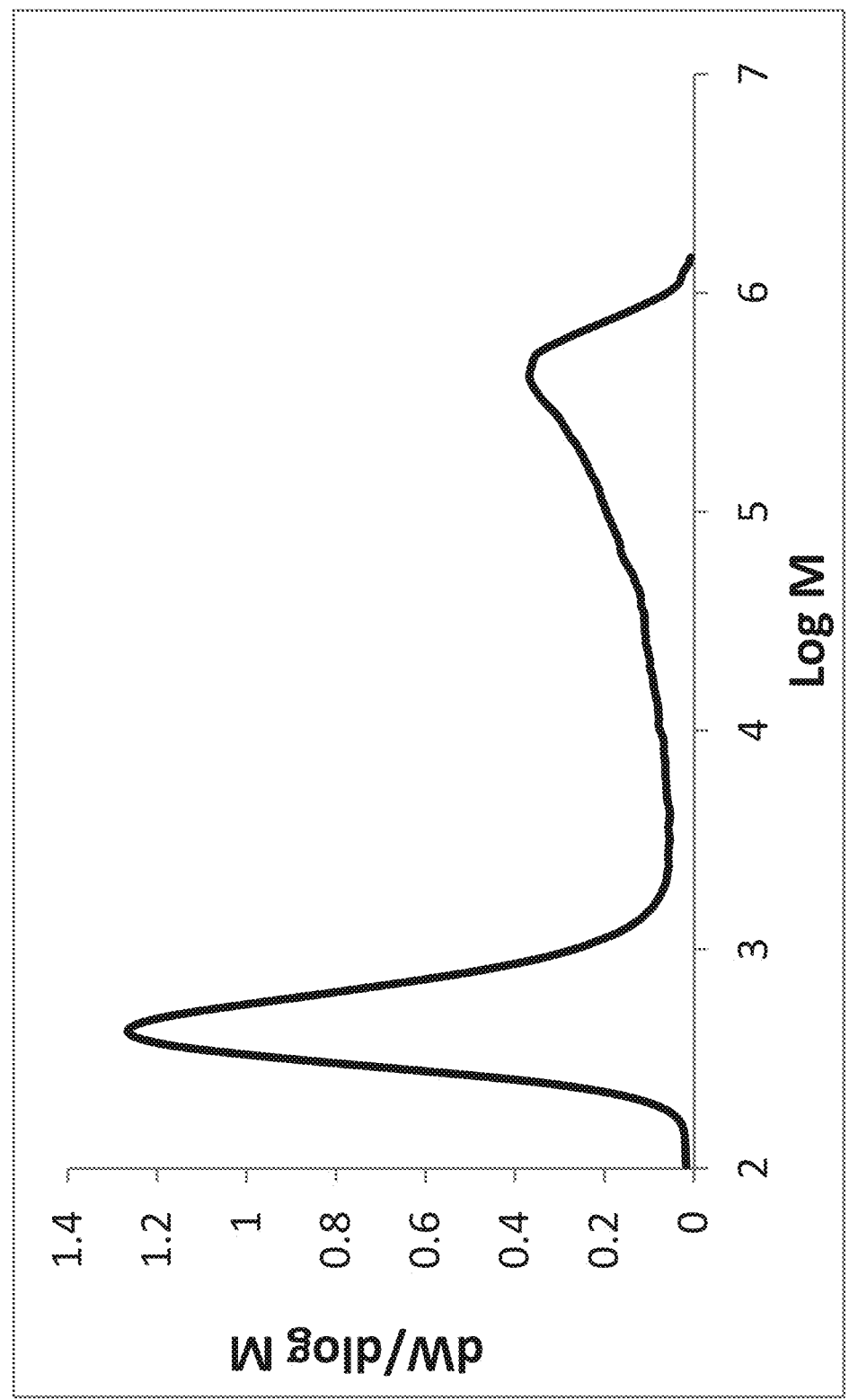
FIG. 4 presents a plot of the molecular weight distribution of the composition of Example 1.

Table I summarizes certain properties and characteristics of a representative composite polymer composition of Example 1, while Table II summarizes certain properties and characteristics of the xylene soluble fraction and the xylene insoluble fraction of the composite polymer composition of Example 1. FIG. 4 illustrates the molecular weight distribution (amount of polymer/oligomer versus the logarithm of molecular weight) for the composite polymer composition of Example 1. Unexpectedly, this polymer composition had a bimodal molecular weight distribution with a surprisingly large distance between the peak molecular weights of the low molecular weight hydrocarbon oligomer component (LMW) component and the high molecular weight hydrocarbon polymer component (HMW) of the composition. The ratio of Mp of the HMW component to the Mp of the LMW component was almost 1000:1. Also unexpectedly, the ratio of Mw/Mn was 142, indicating an extremely broad molecular weight distribution, as demonstrated graphically in FIG. 4.

Figure 5:
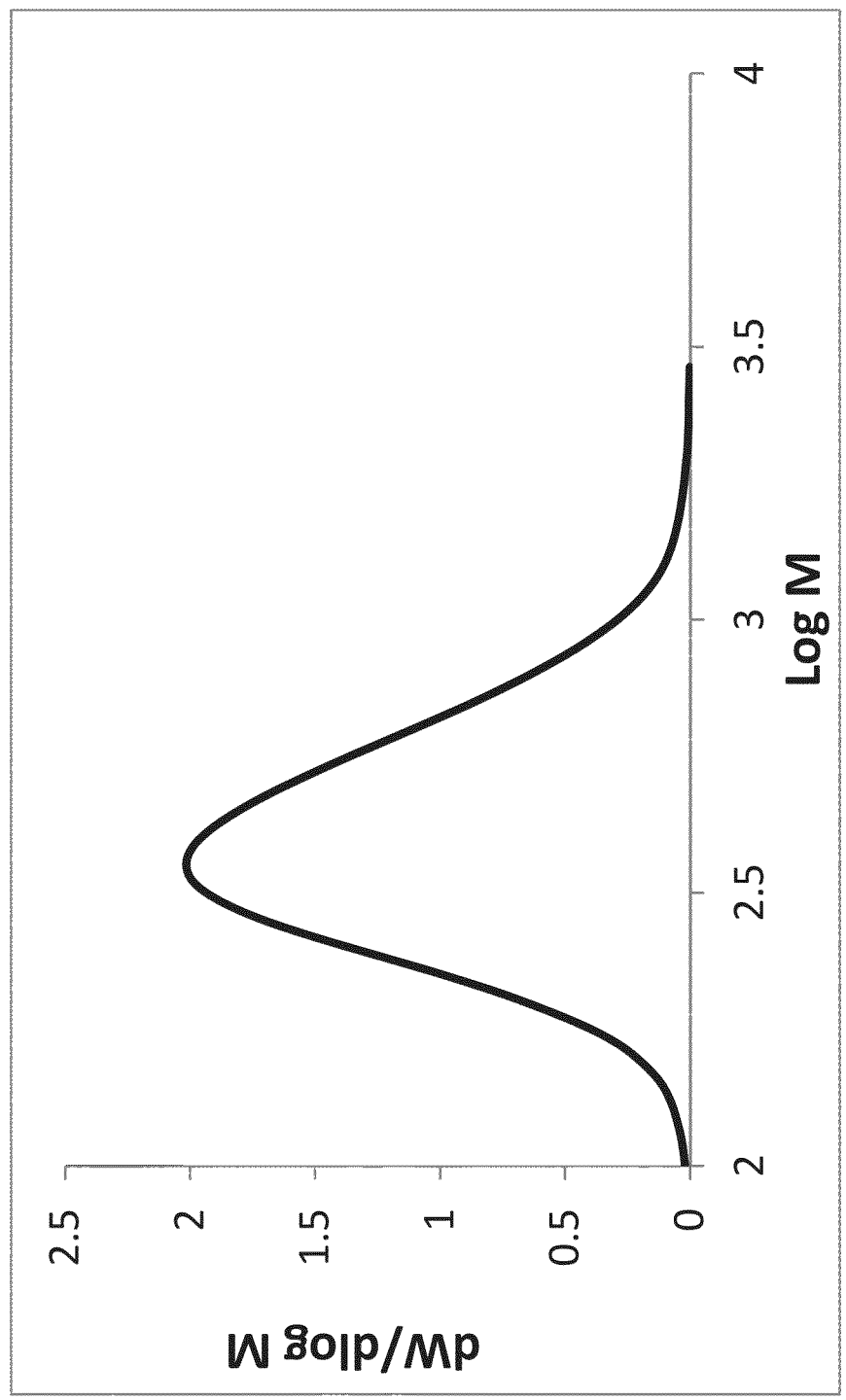
FIG. 5 presents a plot of the molecular weight distribution of the xylene soluble fraction of the composition of Example 1.

The xylene soluble fraction constituted about 46 wt. % of the composite polymer composition, while the xylene insoluble fraction was about 54 wt. %. It should be noted that the xylene soluble fraction is not the same as the low molecular weight hydrocarbon oligomer component and the xylene insoluble fraction is not the same as the high molecular weight hydrocarbon polymer component. Specific molecular weight characteristics of these fractions are shown in Table II, and FIG. 5 illustrates the molecular weight distribution of the xylene soluble fraction of the composition of Example 1. Virtually all of the xylene soluble fraction had a molecular weight of less than 3000 g/mol. The xylene soluble fraction also had a very narrow molecular weight distribution (Mw/Mn<1.5), while the xylene insoluble fraction had a very broad molecular weight distribution (Mw/Mn >40).

Figure 6:
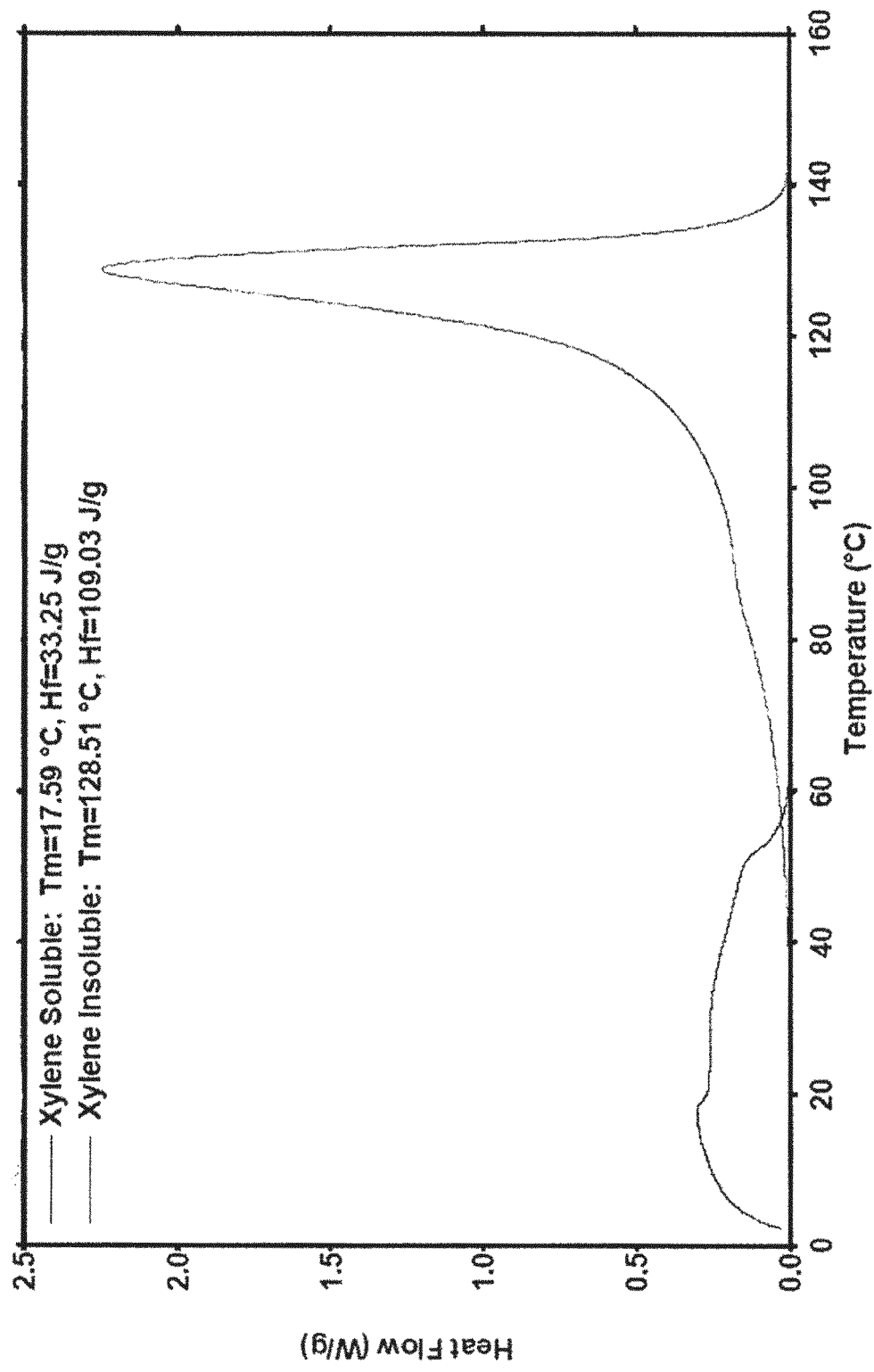
FIG. 6 presents a differential scanning calorimeter (DSC) plot of the xylene soluble fraction and the xylene insoluble fraction of the composition of Example 1.
Figure 7:
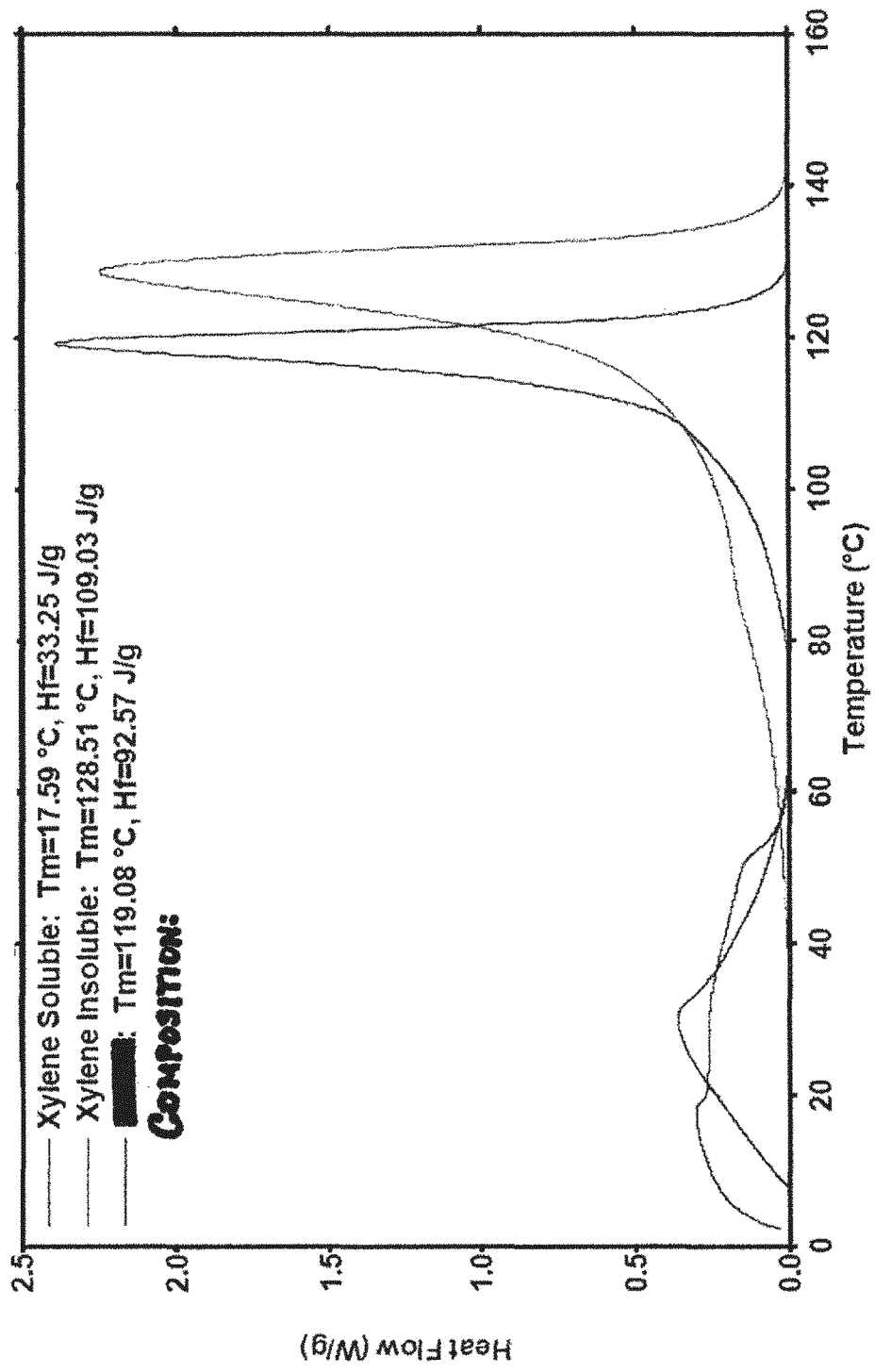
FIG. 7 presents a DSC plot of the composition of Example 1, and the xylene soluble fraction and the xylene insoluble fraction of the composition of Example 1.
Figure 8:
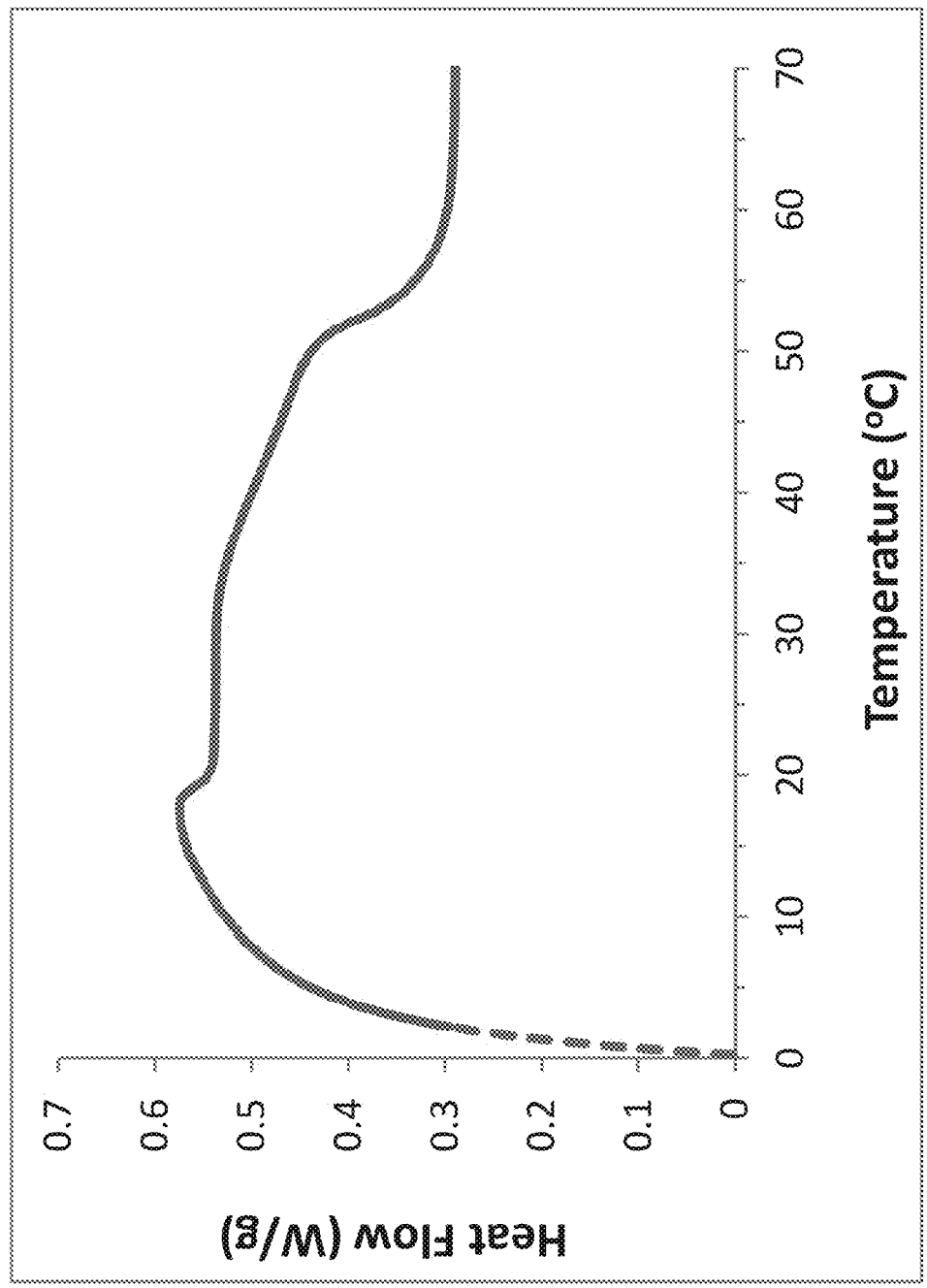
FIG. 8 presents a DSC plot of the xylene soluble fraction of the composition of Example 1.

FIG. 6 illustrates a DSC plot ($2^{nd}$ heat) of the xylene soluble fraction and the xylene insoluble fraction of the composite polymer composition of Example 1, whereas FIG. 7 overlays a DSC plot ($2^{nd}$ heat) of the overall polymer composition. FIG. 8 illustrates an exploded DSC plot ($2^{nd}$ heat) of only the xylene soluble fraction of the composite polymer composition. The peak melting temperature of the xylene insoluble fraction in FIG. 6 was 128° C., while the peak melting temperature of the xylene soluble fraction, surprisingly, was below 25° C. (e.g., peak at 17.6° C.), indicating a large liquid component of the xylene soluble fraction. From these DSC plots, the amount of the liquid component of the overall composition was calculated as 17.9 wt. % (the percentage heat flow area under the xylene soluble fraction DSC curve from a temperature of 2.2° C. to 25° C. based upon a xylene soluble fraction DSC analysis run from 2.2° C. to 69.2° C. was 38.7 wt. %, and the xylene soluble fraction was 46.3 wt. % of the overall composition).

Figure 9:
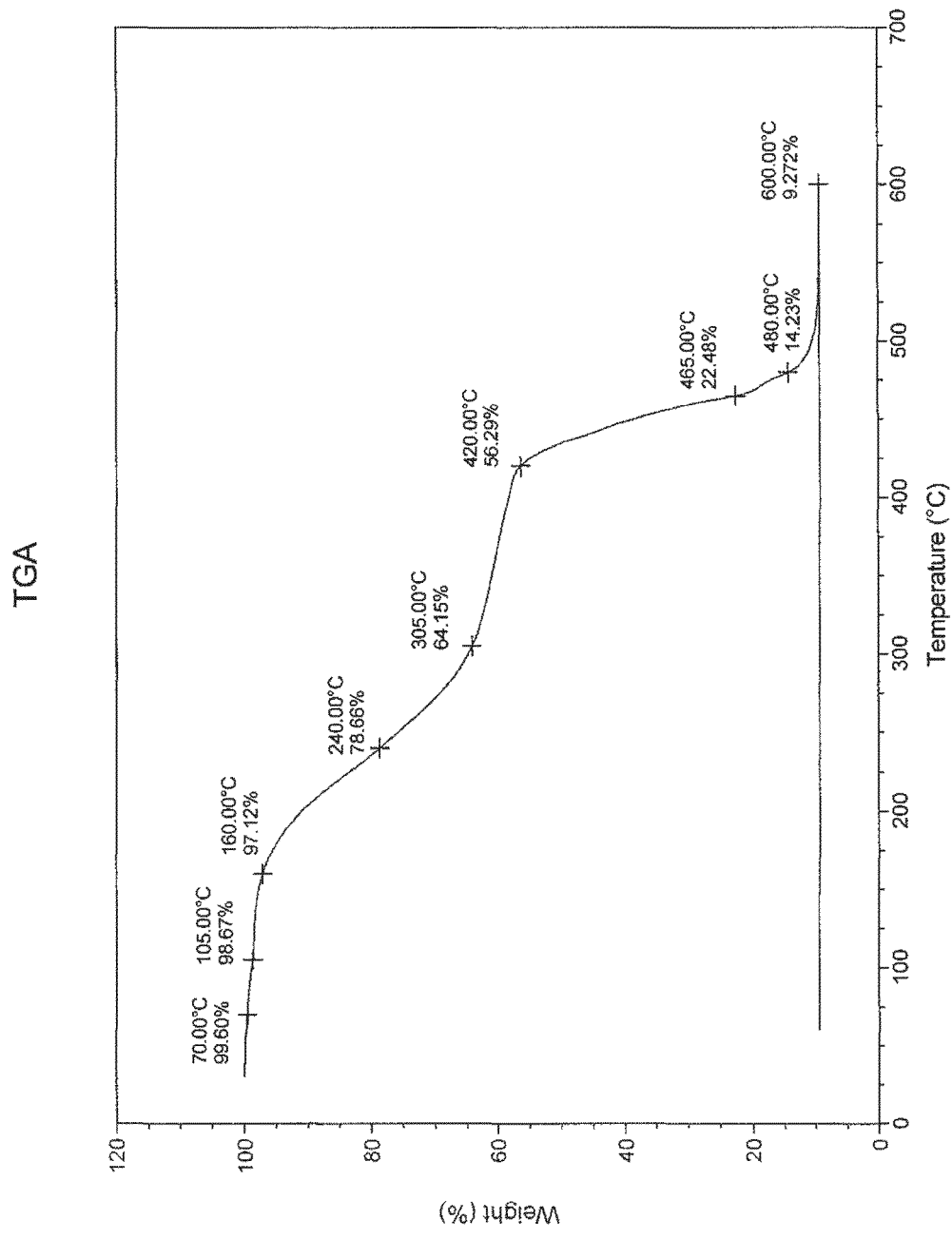
FIG. 9 presents a thermogravimetric analysis (TGA) plot of the composition of Example 1.
Figure 10:
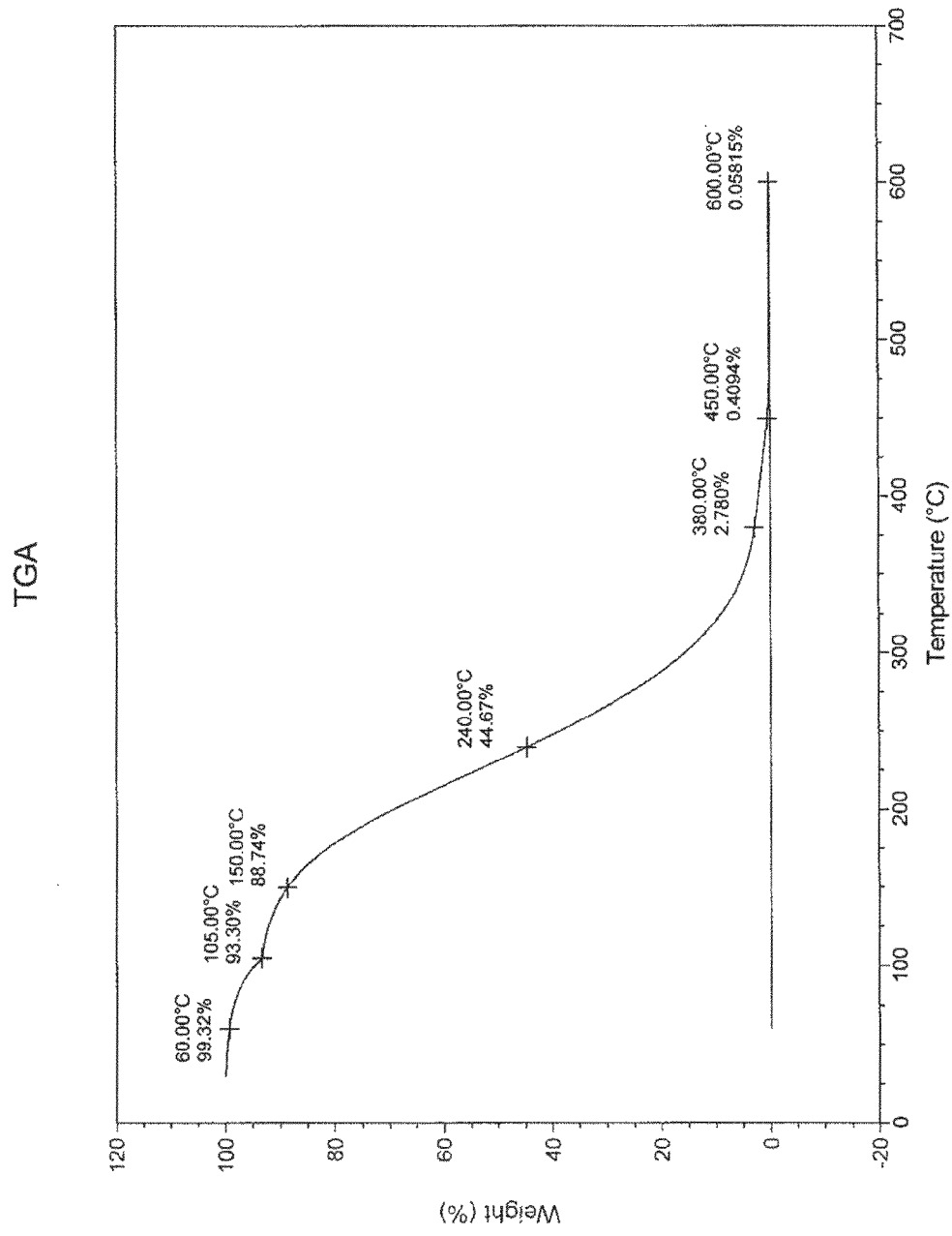
FIG. 10 presents a thermogravimetric analysis (TGA) plot of the xylene soluble fraction of the composition of Example 1.

FIG. 9 illustrates a TGA plot of the composite polymer composition of Example 1, whereas FIG. 10 illustrates a TGA plot of the xylene soluble fraction of the composition polymer composition. From FIG. 9, the amount of the TGA liquid component of the overall composition (weight lost from 0° C. to 240° C.) was 21.3%, while from FIG. 10, the amount of the TGA liquid component in the xylene soluble fraction was 55.3%.

Figure 11:
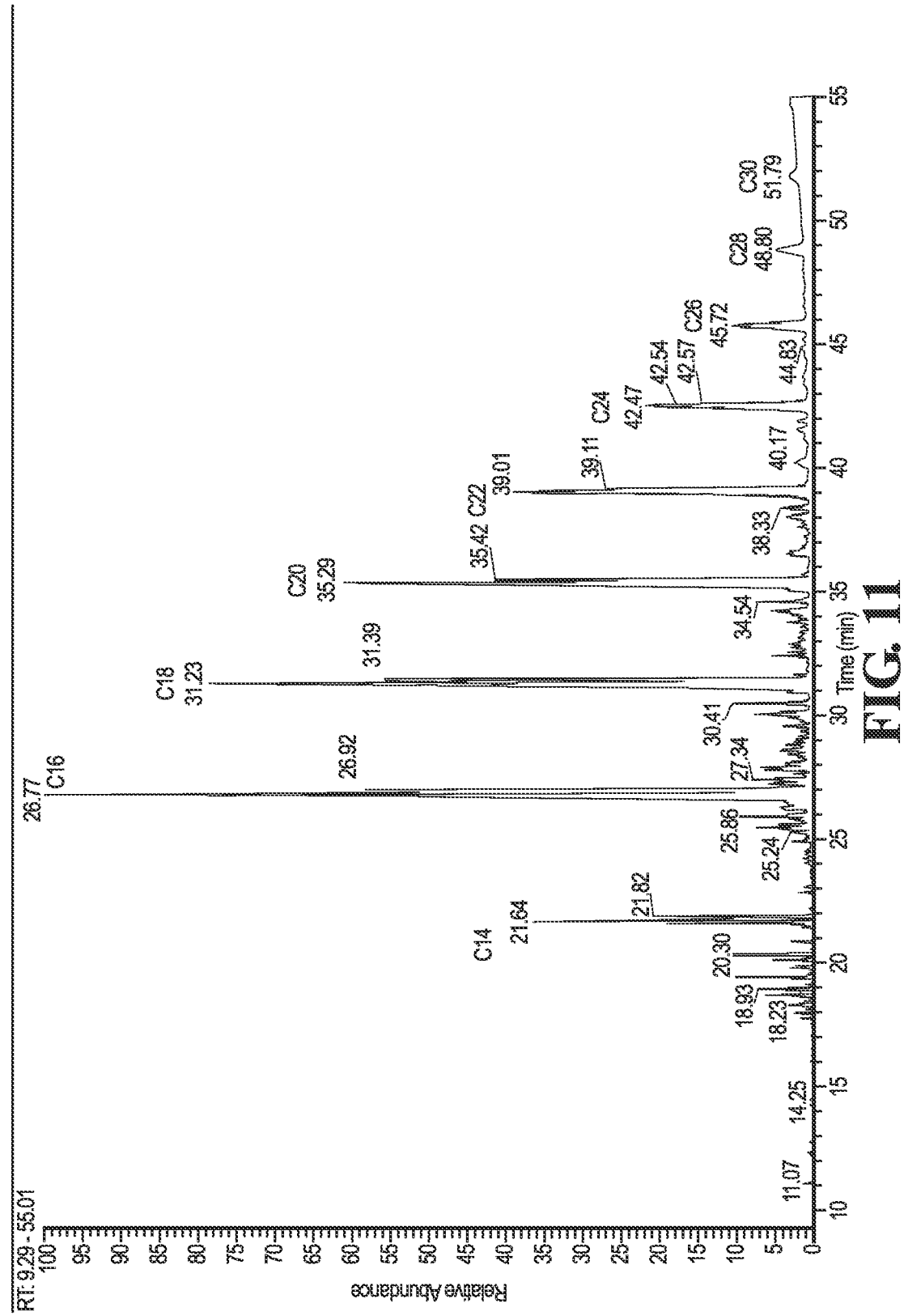
FIG. 11 presents a gas chromatograph-mass spectrometer (GC-MS) plot of the lower molecular weight portion of the xylene soluble fraction of the composition of Example 1.
Figure 12:
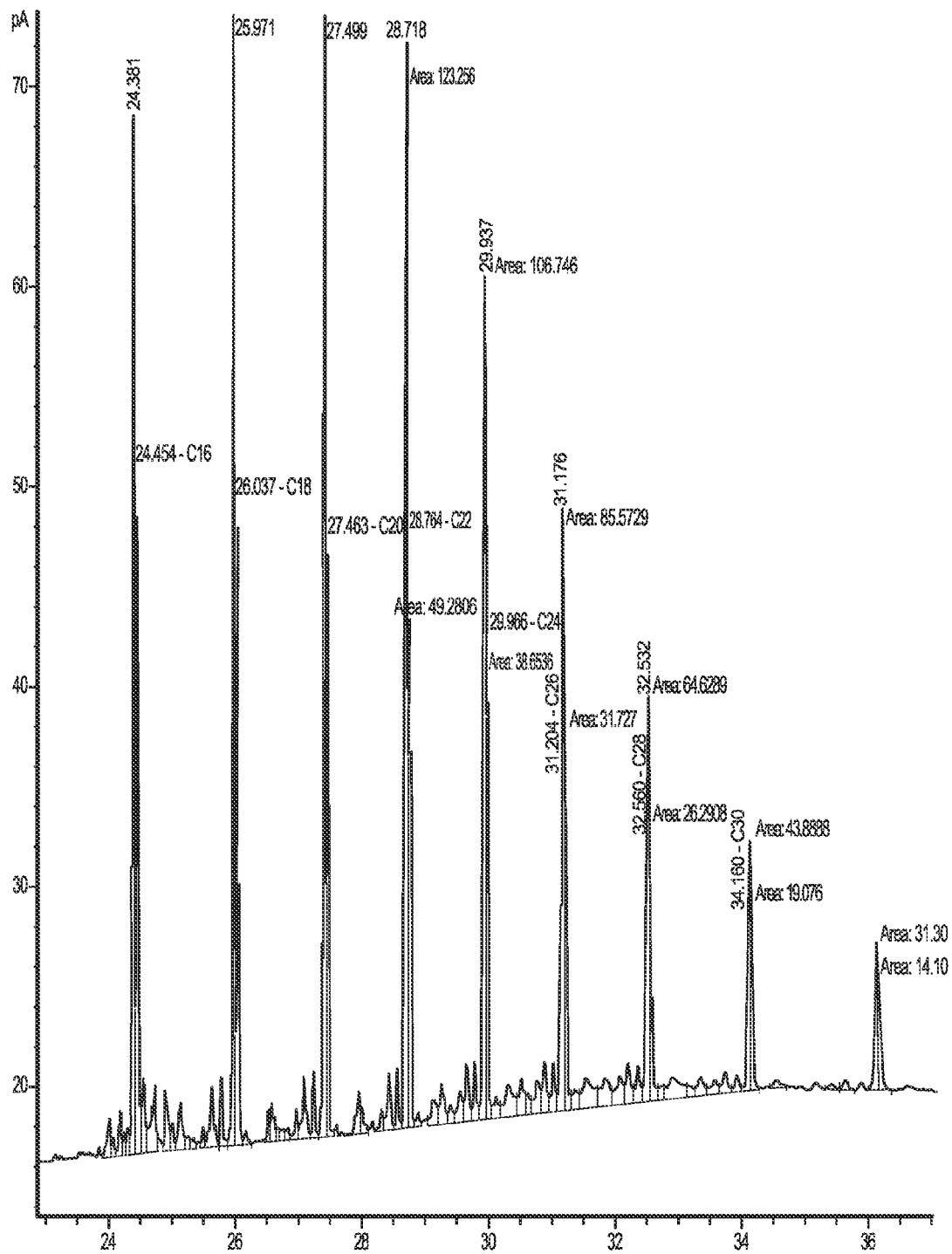
FIG. 12 presents a gas chromatograph (GC) plot of the lower molecular weight portion of the xylene soluble fraction of the composition of Example 1.

FIG. 11 illustrates a GC-MS plot of the lower molecular weight portion of the xylene soluble fraction of the composite polymer composition of Example 1, whereas FIG. 12 illustrates a GC-FID plot of the lower molecular weight portion of the xylene soluble fraction of the composition polymer composition. From the normalized GC-MS results plot (normalization was performed using the GC-FID data), the amount of liquid component in the composite polymer composition (inclusive of any compounds that are liquids, and not gasses or solids, at standard temperature (25° C.) and pressure (1 atm), e.g., up to and including $C_{16}$ saturated compounds and $C_{18}$ olefins) was calculated as 14.9 wt. %.

The amounts of certain residual catalyst system metals, chromium and aluminum, in the composite polymer composition also are listed in Table I. Likely due to the significant metal content in the composition, the overall polymer composition density was about 0.965 g/cm³.

Figure 14:
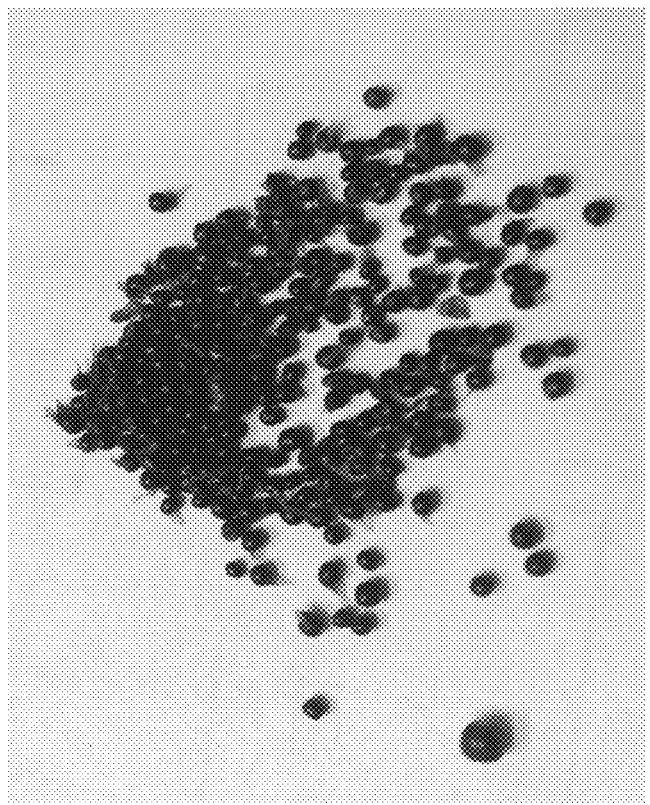
FIG. 14 presents a picture of the polymer composition of Example 1 after pelletizing.
Figure 13:
FIG. 13 presents a picture of the unpelletized polymer composition of Example 1.

FIG. 13 provides a picture of an unpelletized composite polymer composition sample of Example 1, while FIG. 14 provides a picture of a pelletized polymer composition sample of Example 1. Surprisingly, despite the large amount of liquid component of the polymer composition, conventional polymer pellets were able to be produced using conventional pelletizing equipment.

TABLE I

| Example | 1 |
|---|---|
| Mp (LMW), g/mol | 420 |
| Mp (HMW), g/mol | 409,000 |
| Mp (HMW)/Mp (LMW) | 974:1 |
| Mw, g/mol | 108,000 |
| Mz, g/mol | 487,000 |
| Mn, g/mol | 760 |
| Mw/Mn | 142 |
| Mz/Mw | 4.5 |
| Density, g/cm³ | 0.9643 |
| Chromium, wt. % | 0.277 |
| Aluminum, wt. % | 3.63 |
| GC-MS Liquid, wt. % | 14.9 |
| TGA Liquid, wt. % | 21.3 |
| DSC Liquid, wt. % | 17.9 |

TABLE II

| Example 1 | Xylene Soluble Fraction | Xylene Insoluble Fraction |
|---|---|---|
| Weight fraction, wt. % | 46.3 | 53.7 |
| Mp, g/mol | 420 | 404,000 |
| Mw, g/mol | 440 | 225,000 |
| Mw/Mn | 1.22 | 43 |
| Mz, g/mol | 560 | 486,000 |
| Mz/Mw | 1.3 | 2.2 |
| SCB/1000 TC | 85.5 | 1.8 |
| LCB/1000 TC | 0 | ~0.001 |
| Peak Melting, ° C. | 17.6 | 128.5 |

Example 2

Figure 15:
FIG. 15 provides a picture of the polymer composition of Example 2 after processing through a pelletizer.

Example 2 was processed in a manner similar to that of Example 1. However, the polymer composition of Example 2 did not form pellets when subjected to pelletization (the same as Example 1). FIG. 15 provides a picture of the polymer composition after it had been processed through a pelletizer. As can be seen from FIG. 15, the polymer composition did not form pellets. Several samples of this polymer composition were subjected to the vacuum oven liquid test and found to have 63.8 wt. % to 60.2 wt. % liquids. This example shows that pellets may not be formed if the polymer composition contains too much liquid component, TGA liquid component, and/or DSC liquid component.

The invention is described above with reference to numerous aspects and embodiments, and specific examples. Many variations will suggest themselves to those skilled in the art in light of the above detailed description. All such obvious variations are within the full intended scope of the appended claims. Other embodiments of the invention can include, but are not limited to, the following (embodiments are described as "comprising" but, alternatively, can "consist essentially of" or "consist of"):

Embodiment 1

A composition comprising:
a high molecular weight hydrocarbon polymer component and a low molecular weight hydrocarbon oligomer component, wherein a ratio of the Mp of the high molecular weight hydrocarbon polymer component to the Mp of the low molecular weight hydrocarbon oligomer component is in a range from 400:1 to 2000:1; and
a liquid component in a range from 1 wt. % to 35 wt. % of the composition, the liquid component comprising saturated hydrocarbon compounds having 16 or less carbon atoms and unsaturated hydrocarbon compounds having 18 or less carbon atoms.

Embodiment 2

The composition defined in embodiment 1, wherein the weight percentage of the liquid component in the composition is in any range disclosed herein, e.g., from 1 wt. % to 35 wt. %, from 1 wt. % to 30 wt. %, from 1 wt. % to 25 wt. %, from 2 wt. % to 35 wt. %, from 2 wt. % to 25 wt. %, from 5 wt. % to 25 wt. %, etc.

Embodiment 3

A composition comprising:
a high molecular weight hydrocarbon polymer component and a low molecular weight hydrocarbon oligomer component, wherein a ratio of the Mp of the high molecular weight hydrocarbon polymer component to the Mp of the low molecular weight hydrocarbon oligomer component is in a range from 400:1 to 2000:1; and
a TGA liquid component in a range from 1 wt. % to 35 wt. % of the composition.

Embodiment 4

The composition defined in embodiment 3, wherein the weight percentage of the TGA liquid component in the composition is in any range disclosed herein, e.g., from 1 wt. % to 35 wt. %, from 1 wt. % to 30 wt. %, from 1 wt. % to 25 wt. %, from 2 wt. % to 35 wt. %, from 2 wt. % to 25 wt. %, from 5 wt. % to 25 wt. %, etc.

Embodiment 5

A composition comprising:
a high molecular weight hydrocarbon polymer component and a low molecular weight hydrocarbon oligomer component, wherein a ratio of the Mp of the high molecular weight hydrocarbon polymer component to the Mp of the low molecular weight hydrocarbon oligomer component is in a range from 400:1 to 2000:1; and
a DSC liquid component in a range from 1 wt. % to 35 wt. % of the composition.

Embodiment 6

The composition defined in embodiment 5, wherein the weight percentage of the DSC liquid component in the composition is in any range disclosed herein, e.g., from 1 wt. % to 35 wt. %, from 1 wt. % to 30 wt. %, from 1 wt. % to 25 wt. %, from 2 wt. % to 35 wt. %, from 2 wt. % to 25 wt. %, from 5 wt. % to 25 wt. %, etc.

Embodiment 7

The composition defined in any one of embodiments 1-6, wherein a ratio of the Mp of the high molecular weight hydrocarbon polymer component to the Mp of the low molecular weight hydrocarbon oligomer component is any range disclosed herein, e.g., from 500:1 to 1500:1, from 600:1 to 1400:1, from 700:1 to 1300:1, from 800:1 to 1200:1, etc.

Embodiment 8

The composition defined in any one of embodiments 1-7, wherein the low molecular weight hydrocarbon oligomer component has a Mp in any range disclosed herein, e.g., from 200 to 2500, from 250 to 1000, from 250 to 750, from 250 to 600, from 300 to 700, from 350 to 550 g/mol, etc.

Embodiment 9

The composition defined in any one of embodiments 1-8, wherein the high molecular weight hydrocarbon polymer component has a Mp in any range disclosed herein, e.g., from 150,000 to 1,000,000, from 150,000 to 750,000, from 200,000 to 600,000, from 250,000 to 550,000, from 300,000 to 600,000, from 250,000 to 500,000, from 300,000 to 500,000 g/mol, etc.

Embodiment 10

The composition defined in any one of embodiments 1-9, wherein the composition has a ratio of Mw/Mn in any range disclosed herein, e.g., from 50 to 200, from 70 to 170, from 90 to 170, from 80 to 160, from 75 to 150, from 100 to 160, etc.

Embodiment 11

The composition defined in any one of embodiments 1-10, wherein the composition has a ratio of Mz/Mw in any range disclosed herein, e.g., from 3 to 15, from 4 to 14, from 4 to 10, from 5 to 10, etc.

Embodiment 12

The composition defined in any one of embodiments 1-11, wherein the composition has a Mw in any range disclosed herein, e.g., from 25,000 to 250,000, from 30,000 to 130,000, from 40,000 to 120,000, from 60,000 to 160,000 g/mol, etc.

Embodiment 13

The composition defined in any one of embodiments 1-12, wherein the composition has a Mn in any range disclosed herein, e.g., from 200 to 2500, from 300 to 1500, from 400 to 1000, from 400 to 900 g/mol, etc.

Embodiment 14

The composition defined in any one of embodiments 1-13, wherein the composition has a Mz in any range disclosed herein, e.g., from 300,000 to 800,000, from 350,000 to 750,000, from 400,000 to 700,000, from 400,000 to 600,000 g/mol, etc.

Embodiment 15

The composition defined in any one of embodiments 1-14, wherein the composition has a density in any range disclosed herein, e.g., from 0.93 to 1, from 0.94 to 0.99, from 0.935 to 0.995, or from 0.94 to 0.98 g/cm$^3$.

Embodiment 16

The composition defined in any one of embodiments 1-15, wherein the composition has an aluminum content in any range disclosed herein, e.g., from 0.5 wt. % to 6 wt. %, from 0.7 wt. % to 4 wt. %, from 1 wt. % to 4 wt. %, from 1 wt. % to 3 wt. %, from 1 wt. % to 2.5 wt. %, etc.

Embodiment 17

The composition defined in any one of embodiments 1-16, wherein the composition has a chromium content in any range disclosed herein, e.g., from 0.05 wt. % to 1 wt. %, from 0.1 wt. % to 0.5 wt. %, from 0.05 wt. % to 0.4 wt. %, from 0.08 wt. % to 0.3 wt. %, from 0.08 wt. % to 0.2 wt. %, etc.

Embodiment 18

The composition defined in any one of embodiments 1-17, wherein the composition has a bimodal molecular weight distribution.

Embodiment 19

The composition defined in any one of embodiments 1-18, wherein the composition is a single reactor product or single product stream, e.g., a homogeneous mixture, not a blend of two polymeric/oligomeric components, for instance, having different molecular weight characteristics.

Embodiment 20

The composition defined in any one of embodiments 1-19, wherein the high molecular weight hydrocarbon polymer component comprises ethylene/α-olefin copolymers, e.g., polymer chains incorporating various length olefin comonomers.

Embodiment 21

The composition defined in any one of embodiments 1-20, wherein the high molecular weight hydrocarbon polymer component, the low molecular weight hydrocarbon oligomer component, and the liquid component (or TGA liquid component, or DSC liquid component) comprise any weight percentage of the composition disclosed herein, e.g., at least 88 wt. %, at least 90 wt. %, at least 92 wt. %, at least 95 wt. %, at least 96 wt. %, etc.

Embodiment 22

The composition defined in any one of embodiments 1-21, wherein the composition comprises a xylene soluble fraction and a xylene insoluble fraction, and the xylene soluble fraction is in any weight percentage range disclosed herein, e.g., from 30 wt. % to 80 wt. %, from 30 wt. % to 70 wt. %, from 40 wt. % to 80 wt. %, from 35 wt. % to 80 wt. %, from 35 wt. % to 70 wt. %, from 30 wt. % to 60 wt. %, etc. based on the total weight of the composition.

Embodiment 23

The composition defined in embodiment 22, wherein the xylene insoluble fraction comprises ethylene/α-olefin copolymers, e.g., polymer chains incorporating various length olefin comonomers.

Embodiment 24

The composition defined in embodiment 22 or 23, wherein the xylene insoluble fraction has a ratio of Mw/Mn in any range disclosed herein, e.g., from 5 to 100, from 10 to 100, from 20 to 70, from 25 to 100, from 25 to 70, from 30 to 90, from 30 to 60, etc.

Embodiment 25

The composition defined in any one of embodiments 22-24, wherein the xylene insoluble fraction has a DSC peak melting temperature in any range disclosed herein, e.g., from 118 to 134° C., from 122 to 132° C., from 124 to 130° C., etc.

Embodiment 26

The composition defined in any one of embodiments 22-25, wherein the xylene insoluble fraction has a Mp (or Mz) in any range disclosed herein, e.g., from 150,000 to 750,000, from 200,000 to 900,000, from 200,000 to 600,000, from 300,000 to 900,000, from 300,000 to 750,000 g/mol, etc.

Embodiment 27

The composition defined in any one of embodiments 22-26, wherein the xylene insoluble fraction has a Mn in any range disclosed herein, e.g., from 3,800 to 12,000, from 4,000 to 10,000, from 4,000 to 8,000, from 4,500 to 10,000, from 4,500 to 7,500 g/mol, etc.

Embodiment 28

The composition defined in any one of embodiments 22-27, wherein the xylene soluble fraction comprises liquids at standard temperature and pressure, and/or olefin-based oligomers having a Mp in a range from 250 to 1500 g/mol.

Embodiment 29

The composition defined in any one of embodiments 22-28, wherein the xylene soluble fraction has a ratio of Mw/Mn (or Mz/Mw) in any range disclosed herein, e.g., from 1.01 to 3, from 1.05 to 2.5, from 1.01 to 2, from 1.05 to 3, from 1.05 to 2, from 1.1 to 2.5, etc.

Embodiment 30

The composition defined in any one of embodiments 22-29, wherein the xylene soluble fraction has a Mp (or Mn, or Mw, or Mz) in any range disclosed herein, e.g., from 250 to 1500, from 250 to 1000, from 300 to 1500, from 300 to 1000, from 350 to 1250, from 350 to 750 g/mol, etc.

Embodiment 31

The composition defined in any one of embodiments 22-30, wherein the xylene soluble fraction has a DSC peak melting temperature in any range disclosed herein, e.g., from 10 to 60° C., from 10 to 50° C., from 10 to 40° C., from 10 to 35° C., etc.

Embodiment 32

The composition defined in any one of embodiments 1-31, wherein the composition is in the form of pellets.

Embodiment 33

The composition defined in any one of embodiments 1-32, further comprising any additive disclosed herein, e.g., an antioxidant, an acid scavenger, an antiblock additive, a slip additive, a colorant, a filler, a polymer processing aid, a UV inhibitor or stabilizer, etc., or any combination thereof.

Embodiment 34

An article comprising the composition defined in any one of embodiments 1-33.

Embodiment 35

An article comprising the composition defined in any one of embodiments 1-33, wherein the article is an agricultural film, an automobile part, a bottle, a drum, a fiber or fabric, a food packaging film or container, a food service article, a fuel tank, a geomembrane, a household container, a liner, a molded product, a medical device or material, a pipe, a sheet or tape, or a toy.

Embodiment 36

A process comprising:
(1) contacting ethylene, a catalyst system comprising a transition metal compound and a metal alkyl, and an optional oligomerization diluent in a reactor under oligomerization conditions to form an oligomer product;
(2) removing a reactor effluent from the reactor;
(3) deactivating the catalyst system (e.g., to produce a deactivated reactor effluent);

(4) isolating a heavies stream comprising a liquid fraction and a solid fraction; and (5) removing at least a portion of the liquid fraction from the heavies stream to produce a polymer composition.

Embodiment 37

The process defined in embodiment 36, wherein the heavies stream is isolated by (I) removing at least a portion of a gaseous fraction from the reactor effluent (or the deactivated reactor effluent), (II) removing at least a portion of a liquid fraction from the reactor effluent (or the deactivated reactor effluent), or a combination thereof, using one or more separation steps.

Embodiment 38

The process defined in embodiment 36 or 37, wherein the reactor effluent (or the deactivated reactor effluent) comprises:
(i) ethylene;
(ii) an oligomer product comprising:
  (a) a light oligomer;
  (b) a specified oligomer that is at least 70 wt. % of the oligomer product, the specified oligomer comprising hexenes, octenes, or a combination thereof;
  (c) a heavy oligomer; and
  (d) a polymer; and
(iii) the optional oligomerization diluent.

Embodiment 39

The process defined in embodiment 38, wherein the heavies stream is isolated by removing (I) at least a portion of the ethylene, (II) at least a portion of the light oligomer, (III) at least a portion of the specified oligomer, (IV) at least a portion of the heavy oligomer, (V) at least a portion of the optional oligomerization diluent, or (VI) any combination of (I) to (V), from the reactor effluent (or the deactivated reactor effluent) using one or more separation steps.

Embodiment 40

The process defined in embodiment 37 or 39, wherein the one or more separation steps comprise a flash process, a distillation process, or combinations thereof.

Embodiment 41

The process defined in any one of embodiments 36-40, wherein the heavies stream comprises the liquid fraction and the solid fraction, and the solid fraction is any weight percentage of the heavies stream disclosed herein, e.g., from 5 to 35 wt. %, from 5 to 25 wt. %, from 5 to 20 wt. %, etc.

Embodiment 42

The process defined in embodiment 41, wherein the solid fraction of the heavies stream comprises all or a portion of a heavy solid oligomer, all or a portion of the polymer, or any combination thereof.

Embodiment 43

The process defined in any one of embodiments 36-42, wherein the heavies stream comprises the liquid fraction and the solid fraction, and the liquid fraction is any weight percentage of the heavies stream disclosed herein, e.g., from 65 to 95 wt. %, from 75 to 95 wt. %, from 80 to 95 wt. %, etc.

Embodiment 44

The process defined in embodiment 43, wherein the liquid fraction of the heavies stream comprises all or a portion of a heavy liquid oligomer, all or a portion of the optional oligomerization diluent, or any combination thereof.

Embodiment 45

The process defined in any one of embodiments 38-44, wherein the weight percentage of the polymer in the heavies stream is any weight percentage of the polymer in the heavies stream disclosed herein, e.g., from 2 to 19 wt. %, from 2 to 18 wt. %, from 3 to 17 wt. %, etc.

Embodiment 46

The process defined in any one of embodiments 38-45, wherein the weight percentage of the heavy oligomer in the heavies stream is any weight percentage of the heavy oligomer in the heavies stream disclosed herein, e.g., from 35 to 80 wt. %, from 35 to 70 wt. %, from 40 to 75 wt. %, etc.

Embodiment 47

The process defined in any one of embodiments 38-46, wherein the weight percentage of the oligomerization diluent in the heavies stream, when utilized, is any weight percentage of the oligomerization diluent in the heavies stream disclosed herein, e.g., from 1 to 25 wt. %, from 5 to 25 wt. %, from 2 to 20 wt. %, etc.

Embodiment 48

The process defined in any one of embodiments 38-47, wherein the maximum amount of ethylene in the heavies stream is any maximum amount of ethylene in the heavies stream disclosed herein, e.g., a maximum of 15 wt. %, 10 wt. %, 5 wt. %, 1 wt. %, 0.5 wt. %, etc.

Embodiment 49

The process defined in any one of embodiments 38-48, wherein the maximum amount of the light oligomer in the heavies stream is any maximum amount of the light oligomer in the heavies stream disclosed herein, e.g., a maximum of 15 wt. %, 10 wt. %, 5 wt. %, 1 wt. %, 0.5 wt. %, etc.

Embodiment 50

The process defined in any one of embodiments 38-49, wherein the maximum amount of the specified oligomer in the heavies stream is any maximum amount of the specified oligomer in the heavies stream disclosed herein, e.g., a maximum of 15 wt. %, 10 wt. %, 5 wt. %, 1 wt. %, etc.

Embodiment 51

The process defined in any one of embodiments 38-50, wherein the maximum amount of the total of the ethylene, light oligomer, and specified oligomer in the heavies stream is any maximum amount of the total of the ethylene, light oligomer, and specified oligomer in the heavies stream disclosed herein, e.g., 15 wt. %, 10 wt. %, 5 wt. %, 1 wt. %, etc.

Embodiment 52

The process defined in any one of embodiments 36-51, wherein at least a portion of the oligomerization diluent is removed from the heavies stream to produce the polymer composition.

Embodiment 53

The process defined in any one of embodiments 38-52, wherein at least a portion of the heavy oligomer (e.g., at least a portion of the heavy liquid oligomer) is removed from the heavies stream to produce the polymer composition.

Embodiment 54

The process defined in any one of embodiments 36-53, wherein at least a portion of the liquid fraction is removed from the heavies stream by an evaporation and/or distillation process.

Embodiment 55

The process defined in embodiment 54, wherein the evaporation and/or distillation process is i) operated at any temperature greater than 20° C. disclosed herein, ii) operated at any pressure below atmospheric pressure disclosed herein, iii) is operated in a manner wherein the heavies stream has an average residence time of less than one hour in the evaporation and/or distillation process device, or i) any combination thereof.

Embodiment 56

The process defined in embodiment 54 or 55, wherein the evaporation and/or distillation process is conducted in a thin film evaporator, a wiped film evaporator, a short-path evaporator, or a combination thereof.

Embodiment 57

The process defined in any one of embodiments 36-56, wherein the polymer composition is defined in any one of embodiments 1-31.

Embodiment 58

The process defined in any one of embodiments 36-56, wherein the polymer composition is characterized by (a) a high molecular weight hydrocarbon polymer component and a low molecular weight hydrocarbon oligomer component, wherein a ratio of the Mp of the high molecular weight hydrocarbon polymer component to the Mp of the low molecular weight hydrocarbon oligomer component is in a range from 400:1 to 2000:1; and (b) a liquid component in a range from 1 wt. % to 35 wt. % of the composition, the liquid component comprising saturated hydrocarbon compounds having 16 or less carbon atoms and unsaturated hydrocarbon compounds having 18 or less carbon atoms (or a TGA liquid component in a range from 1 wt. % to 35 wt. % of the composition, or a DSC liquid component in a range from 1 wt. % to 35 wt. % of the composition.

Embodiment 59

The process defined in any one embodiments 36-58, wherein the reactor effluent further comprises catalyst system components.

Embodiment 60

The process defined in any one of embodiments 36-59, wherein the reactor effluent further comprises metal catalyst system components.

Embodiment 61

The process defined in any one of embodiment 36-60, wherein deactivating the catalyst system comprises contacting the reactor effluent with any suitable catalyst system deactivating agent disclosed herein and/or subjecting the reactor effluent to any suitable process steps to deactivate the catalyst system disclosed herein.

Embodiment 62

The process defined in embodiment 61, wherein the catalyst deactivating agent comprises any suitable alcohol compound disclosed herein (e.g., 2-ethylhexanol), any suitable amine compound disclosed herein, or any combination of any alcohol compound disclosed herein and any amine compound disclosed herein.

Embodiment 63

The process defined in any one of embodiments 36-62, wherein the heavies stream further comprises metal catalyst system components, deactivated metal catalyst system components, or any combination thereof.

Embodiment 64

The process defined in any one of embodiments 36-63, wherein the polymer composition comprises metal catalyst system components, deactivated metal catalyst system components, or any combination thereof.

Embodiment 65

The process defined in any one of embodiments 36-64, wherein the polymer composition has any chromium content disclosed herein, e.g., from 0.05 wt. % to 0.4 wt. %, from 0.05 wt. % to 0.25 wt. %, from 0.08 wt. % to 0.2 wt. %, etc.

Embodiment 66

The process defined in any one of embodiments 36-65, wherein the polymer composition has any aluminum content disclosed herein, e.g., from 0.5 wt. % to 6 wt. %, from 0.7 wt. % to 3 wt. %, from 1 wt. % to 2.5 wt. %, etc.

Embodiment 67

The process defined in any one of embodiments 36-63, wherein prior to removing a portion of the liquid fraction from the heavies stream, at least a portion (e.g., substantially all) of the metal catalyst system components and/or deactivated metal catalyst system components is removed from the heavies stream.

Embodiment 68

The process defined in embodiment 67, wherein prior to removing a portion of the liquid fraction from the heavies stream, the heavies stream is subjected to further process steps comprising:

(i) contacting the heavies stream with an aqueous solution to form a hydrocarbon/water mixture; and (ii) separating the hydrocarbon/water mixture into (a) an aqueous phase comprising the portion (or substantially all) of the metal catalyst system components and/or deactivated metal catalyst system components, and (b) a hydrocarbon phase comprising hydrocarbon components of the heavies stream.

Embodiment 69

The process defined in any one of embodiments 36-63, wherein prior to isolating the heavies stream, at least a portion (e.g., substantially all) of the metal catalyst system components and/or deactivated metal catalyst system components is removed from the reactor effluent (or the deactivated reactor effluent).

Embodiment 70

The process defined in embodiment 69, wherein the reactor effluent (or the deactivated reactor effluent) is subjected to further process steps comprising:

(i) contacting the reactor effluent (or the deactivated reactor effluent) with an aqueous solution to form an hydrocarbon/water mixture; and (ii) separating the hydrocarbon/water mixture into (a) an aqueous phase comprising the portion (or substantially all) of the metal catalyst system components and/or deactivated metal catalyst system components, and (b) a hydrocarbon phase comprising hydrocarbon components of the reactor effluent (or the deactivated reactor effluent).

Embodiment 71

The process defined in any one of embodiments 36-63, wherein, prior to pelletizing, at least a portion (e.g., substantially all) of the metal catalyst system components and/or deactivated metal catalyst system components is removed from the polymer composition.

Embodiment 72

The process defined in embodiment 71, wherein the polymer composition is subjected to further process steps comprising:

(i) contacting the polymer composition with an aqueous solution to form an hydrocarbon/water mixture; and (ii) separating the hydrocarbon/water mixture into (a) an aqueous phase comprising the portion (or substantially all) of the metal catalyst system components and/or deactivated metal catalyst system components, and (b) a hydrocarbon phase comprising hydrocarbon components of the polymer composition.

Embodiment 73

The process defined in any one of embodiments 68, 70, or 72, wherein the aqueous solution comprises any aqueous Group I metal hydroxide solution or aqueous mineral acid solution disclosed herein.

Embodiment 74

The process defined in any one of embodiments 68, 70, 72, or 73, wherein the hydrocarbon phase is dried by passing the hydrocarbon phase through a water absorbent.

Embodiment 75

The process defined in any one of embodiments 68, 70, or 72-74, wherein the hydrocarbon phase is substantially devoid of chromium and/or aluminum.

Embodiment 76

The process defined in any one of embodiments 67-75, wherein the heavies stream and/or the polymer composition are substantially devoid of chromium and/or aluminum.

Embodiment 77

The process defined in any one of embodiments 36-76, further comprising a step of forming polymer pellets from the polymer composition.

Embodiment 78

The process defined in embodiment 77, wherein the step of forming polymer pellets comprises processing the polymer composition through a pelletizing die (e.g., strand, underwater, water ring, etc.) using any suitable apparatus or any apparatus disclosed herein, e.g., an extruder, a single screw extruder, a twin screw extruder, a gear pump, etc.

Embodiment 79

The process defined in embodiment 77 or 78, wherein the step of forming pellets further comprises contacting the polymer composition with any suitable additive or any additive disclosed herein, e.g., an antioxidant, an acid scavenger, an antiblock additive, a slip additive, a colorant, a filler, a polymer processing aid, a UV inhibitor or stabilizer, etc., or any combination thereof, to form polymer pellets containing the additive(s).

Embodiment 80

A method of preparing an article of manufacture, the method comprising forming the article from the polymer pellets defined in any one of embodiments 77-79 via any suitable technique or any technique disclosed herein, e.g., melt processing, extruding, molding, thermoforming, etc., and including combinations thereof.

Embodiment 81

The process or method defined in any one of embodiments 36-80, wherein the transition metal compound comprises a chromium compound, and the metal alkyl comprises an alkylaluminum compound.

Embodiment 82

The process or method defined in any one of embodiments 38-81, wherein:

a) the catalyst system comprises a chromium compound, a pyrrole compound, a metal alkyl compound, and optionally, a halide containing compound, and the specified oligomer comprises hexenes;

b) the catalyst system comprises a chromium compound, a diphosphinoaminyl compound, and a metal alkyl compound, and the specified oligomer comprises hexenes and/or octenes;

c) the catalyst system comprises a chromium complex of a diphosphinoaminyl compound, and a metal alkyl compound, and the specified oligomer comprises hexenes and/or octenes;

d) the catalyst system comprises a chromium compound, an $N^2$-phosphinylamidine compound, and a metal alkyl compound, and the specified oligomer comprises hexenes and/or octenes;

e) the catalyst system comprises a chromium complex of an $N^2$-phosphinylamidine compound, and a metal alkyl compound, and the specified oligomer comprises hexenes and/or octenes;

f) the catalyst system comprises a chromium compound, an $N^2$-phosphinylformamidine compound, and a metal alkyl compound, and the specified oligomer comprises hexenes and/or octenes;

g) the catalyst system comprises a chromium complex of an $N^2$-phosphinylformamidine compound, and a metal alkyl compound, and the specified oligomer comprises hexenes and/or octenes;

h) the catalyst system comprises a chromium compound, an $N^2$-phosphinylguanidine compound, and a metal alkyl compound, and the specified oligomer comprises hexenes and/or octenes;

i) the catalyst system comprises a chromium complex of an $N^2$-phosphinylguanidine compound, and a metal alkyl compound, and the specified oligomer comprises hexenes and/or octenes; or j) any combination thereof Embodiment 83

The process or method defined in any one of embodiments 36-82 wherein the oligomerization diluent comprises any suitable diluent or any diluent disclosed herein, e.g., cyclohexane, etc.

We claim:

1. A composition comprising:
   a high molecular weight hydrocarbon polymer component and a low molecular weight hydrocarbon oligomer component, wherein a ratio of the Mp of the high molecular weight hydrocarbon polymer component to the Mp of the low molecular weight hydrocarbon oligomer component is in a range from 400:1 to 2000:1; and
   a liquid component in a range from 1 wt. % to 35 wt. % of the composition, the liquid component comprising saturated hydrocarbon compounds having 16 or less carbon atoms and unsaturated hydrocarbon compounds having 18 or less carbon atoms; wherein
   the composition has a Mw in range from 25,000 to 250,000 g/mol.

2. The composition of claim 1, wherein the composition is further characterized by a TGA liquid component in a range from 1 wt. % to 35 wt. % of the composition.

3. The composition of claim 1, wherein the composition is further characterized by a DSC liquid component in a range from 1 wt. % to 35 wt. % of the composition.

4. The composition of claim 1, wherein:
   the low molecular weight hydrocarbon oligomer component has a Mp in a range from 250 to 1000 g/mol; and
   the high molecular weight hydrocarbon polymer component has a Mp in a range from 150,000 to 1,000,000 g/mol.

5. The composition of claim 1, wherein:
   the ratio of the Mp of the high molecular weight hydrocarbon polymer component to the Mp of the low molecular weight hydrocarbon oligomer component is in a range from 600:1 to 1400:1;
   the composition has a ratio of Mw/Mn in a range from 50 to 200; and
   the composition has a Mw in range from 60,000 to 160,000 g/mol.

6. The composition of claim 1, wherein the composition has a density in a range from 0.93 to 1.01 g/cm$^3$, and wherein the composition has:
   an aluminum content in a range from 0.5 wt. % to 6 wt. %; and
   a chromium content in a range from 0.05 wt. % to 1 wt. %.

7. The composition of claim 1, wherein the composition has a bimodal molecular weight distribution.

8. The composition of claim 1, wherein the composition comprises a xylene soluble fraction and a xylene insoluble fraction, and wherein:
   the xylene soluble fraction is from 30 wt. % to 80 wt. % of the composition;
   the xylene soluble fraction has a ratio of Mw/Mn in a range from 1.05 to 2.5;
   the xylene soluble fraction has a DSC peak melting temperature in a range from 10 to 40° C.; and
   the xylene insoluble fraction has a ratio of Mw/Mn in a range from 10 to 100.

9. The composition of claim 8, wherein the xylene soluble fraction has an Mp in a range from 250 to 1500 g/mol.

10. The composition of claim 1, wherein the composition is in the form of pellets.

11. The composition of claim 1, wherein the composition further comprises an additive selected from an antioxidant, an acid scavenger, an antiblock additive, a slip additive, a colorant, a filler, a polymer processing aid, a UV inhibitor or stabilizer, or any combination thereof.

12. An article of manufacture comprising the composition of claim 1.

13. A process for producing the composition of claim 1, comprising:
   (1) contacting ethylene, a catalyst system comprising a transition metal compound and a metal alkyl, and an optional oligomerization diluent in a reactor under oligomerization conditions to form an oligomer product;
   (2) removing a reactor effluent from the reactor;
   (3) deactivating the catalyst system;
   (4) isolating a heavies stream comprising a liquid fraction and a solid fraction; and
   (5) removing at least a portion of the liquid fraction from the heavies stream to produce the composition.

14. The process of claim 13, wherein the reactor effluent comprises:
   (i) ethylene;
   (ii) an oligomer product comprising:
      (a) a light oligomer;
      (b) a specified oligomer that is at least 70 wt. % of the oligomer product, the specified oligomer comprising hexenes, octenes, or a combination thereof;
      (c) a heavy oligomer; and
      (d) a polymer; and
   (iii) the optional oligomerization diluent.

15. The process of claim 14, wherein the heavies stream is isolated by removing (I) at least a portion of the ethylene, (II) at least a portion of the light oligomer, (III) at least a portion of the specified oligomer, (IV) at least a portion of the heavy oligomer, (V) at least a portion of the optional oligomerization diluent, or (VI) any combination of (I) to (V), from the reactor effluent using one or more separation steps.

16. The process of claim 15, wherein at least a portion of the optional oligomerization diluent and at least a portion of the heavy oligomer is removed from the heavies stream by an evaporation and/or distillation process to produce the composition.

17. The process of claim 16, wherein the evaporation and/or distillation process is conducted in a thin film evaporator, a wiped film evaporator, a short-path evaporator, or a combination thereof.

18. The process of claim 13, wherein the transition metal compound comprises a chromium compound, and the metal alkyl comprises an alkylaluminum compound.

19. The process of claim 13, further comprising a step of forming pellets from the composition.

20. The process of claim 19, wherein the step of forming pellets comprises processing the composition through a pelletizing die using an extruder or gear pump.

21. The process of claim 19, wherein the reactor effluent comprises:
    (i) ethylene;
    (ii) an oligomer product comprising:
        (a) a light oligomer;
        (b) a specified oligomer that is at least 70 wt. % of the oligomer product, the specified oligomer comprising hexenes, octenes, or a combination thereof;
        (c) a heavy oligomer; and
        (d) a polymer; and
    (iii) the oligomerization diluent.

22. The process of claim 21, wherein:
    the step of deactivating the catalyst system comprises contacting the reactor effluent with a catalyst system deactivating agent; and
    the composition has an aluminum content in a range from 0.5 wt. % to 6 wt. %, and a chromium content in a range from 0.05 wt. % to 1 wt. %.

* * * * *